United States Patent
Schumperli et al.

(10) Patent No.: US 10,465,191 B2
(45) Date of Patent: Nov. 5, 2019

(54) TRICYCLO-DNA ANTISENSE OLIGONUCLEOTIDES, COMPOSITIONS, AND METHODS FOR THE TREATMENT OF DISEASE

(71) Applicants: ASSOCIATION INSTITUT DE MYOLOGIE, Paris (FR); SORBONNE UNIVERSITE, Paris (FR); UNIVERSITAT BERN, Bern (CH); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Daniel Schumperli, Bern (CH); Christian Leumann, Bern (CH); Denis Furling, Paris (FR); Luis Garcia, Bailly (FR); Thomas Voit, London (GB)

(73) Assignees: ASSOCIATION INSTITUT DE MYOLOGIE, Paris (FR); SORBONNE UNIVERSITE, Paris (FR); UNIVERSITAT BERN, Bern (CH); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 15/428,385

(22) Filed: Feb. 9, 2017

(65) Prior Publication Data
US 2017/0260524 A1 Sep. 14, 2017

Related U.S. Application Data

(62) Division of application No. 13/263,949, filed as application No. PCT/EP2010/054735 on Apr. 9, 2010, now abandoned.

(60) Provisional application No. 61/212,384, filed on Apr. 10, 2009.

(51) Int. Cl.
| | |
|---|---|
| *C12N 15/113* | (2010.01) |
| *A61K 31/711* | (2006.01) |
| *A61K 31/712* | (2006.01) |
| *C12N 15/11* | (2006.01) |

(52) U.S. Cl.
CPC .......... *C12N 15/113* (2013.01); *A61K 31/711* (2013.01); *A61K 31/712* (2013.01); *C12N 15/111* (2013.01); *C12N 2310/11* (2013.01); *C12N 2310/3231* (2013.01); *C12N 2320/33* (2013.01)

(58) Field of Classification Search
CPC . C12N 15/111; C12N 15/113; C12N 2310/11; C12N 2310/3231; C12N 2320/133; A61K 31/712
USPC ........... 435/6.1, 6.11, 91.1, 91.31, 455, 375; 514/44; 536/23.1, 24.5
See application file for complete search history.

(56) References Cited

U.S. PATENT DOCUMENTS

| | | | |
|---|---|---|---|
| 7,807,816 B2 | 10/2010 | Wilton et al. | |
| 8,361,979 B2 | 1/2013 | Aartsma-Rus et al. | |
| 2007/0292408 A1* | 12/2007 | Singh | C12N 15/113 424/130.1 |
| 2009/0076246 A1* | 3/2009 | van Deutekom | A61K 48/0016 530/358 |
| 2010/0125099 A1* | 5/2010 | 't Hoen | A61K 38/185 514/44 A |
| 2010/0184833 A1* | 7/2010 | De Kimpe | C12N 15/113 514/44 R |

(Continued)

FOREIGN PATENT DOCUMENTS

| | | |
|---|---|---|
| WO | 2004/083446 A2 | 9/2004 |
| WO | 2007/002390 A2 | 1/2007 |

(Continued)

OTHER PUBLICATIONS

Ittig et al Nucleic Acids Res., vol. 32, No. 1, pp. 346-353 (2004).*

(Continued)

*Primary Examiner* — Jane J Zara
(74) *Attorney, Agent, or Firm* — Arrigo, Lee, Guttman & Mouta-Bellum LLP

(57) ABSTRACT

Provided are tricyclo-DNA (tc-DNA) AON and methods employing tc-DNA AON for modifying splicing events that occur during pre-mRNA processing. Tricyclo-DNA (tc-DNA) AON are described that may be used to facilitate exon skipping or to mask intronic silencer sequences and/or terminal stein-loop sequences during pre-mRNA processing and to target RNase-mediated destruction of processed mRNA. Tc-DNA AON described herein may be used in methods for the treatment of Duchenne Muscular Dystrophy by skipping a mutated exon 23 or exon 51 within a dystrophin gene to restore functionality of a dystrophin protein; in methods for the treatment of Spinal Muscular Atrophy by masking an intronic silencing sequence and/or a terminal stem-loop sequence within an SMN2 gene to yield modified functional SMN2 protein, including an amino acid sequence encoded by exon 7, which is capable of at least partially complementing a non-functional SMN1 protein; and in methods for the treatment of Steinert's Myotonic Dystrophy by targeting the destruction of a mutated DM1 mRNA comprising 3'-terminal CUG repeats.

15 Claims, 28 Drawing Sheets
Specification includes a Sequence Listing.

(56) References Cited

U.S. PATENT DOCUMENTS

| | | | |
|---|---|---|---|
| 2010/0216238 A1* | 8/2010 | Baker | C12N 15/111 |
| | | | 435/375 |
| 2012/0077860 A1* | 3/2012 | Garcia | C12N 15/86 |
| | | | 514/44 A |

FOREIGN PATENT DOCUMENTS

| | | | |
|---|---|---|---|
| WO | 2008/018795 A1 | | 2/2008 |
| WO | WO 2009/117589 | * | 3/2009 |
| WO | 2009/117589 A1 | | 9/2009 |

OTHER PUBLICATIONS

Leumann, C. J., Nucleic Acids Sympos., Series No. 50, pp. 55-56 (2006).*

European Patent Office, International Search Report for International Application No. PCT/EP2010/054735 dated Jul. 2010.

Heemskerk et al. "In Vivo comparison of 2'-0-methly phosphorothioate and morpholino antisense oligonucleotides for Duchenne muscular dystrophy exon skipping." J. of Gene Med. vol. 11. 2009. pp. 257-266.

Ittig et al. "Nuclear antisense effects in cyclophilin A pre-mRNA splicing by oligonucleotides: a comparison of tricycle-DNA with LNA." Nucleic Acids Res. vol. 32. No. 1. 2004. pp. 346-353.

Leumann. "Sugar modification as a means to increase the biological performance of oligonucleotides." Nucleic Acids Symposium Series. No. 50 2006. pp. 55-56.

Goyenvalle et al., Functional correction in mouse models of muscular dystrophy using exon-skipping tricyclo-DNA oligomers, Nature Medicine volume 21(3): 270-278, Mar. 2015.

* cited by examiner

SEQUENCE LISTING

<160> NUMBER OF SEQ ID NOS: 22

<210> SEQ ID NO 1
<211> LENGTH: 15
<212> TYPE: DNA
<213> ORGANISM: Artificial Sequence
<220> FEATURE:
<223> OTHER INFORMATION: tc-DNA AON M23D (+02-13)

<400> SEQUENCE: 1
aacctcggct tacct                                                        15

<210> SEQ ID NO 2
<211> LENGTH: 15
<212> TYPE: DNA
<213> ORGANISM: Artificial Sequence
<220> FEATURE:
<223> OTHER INFORMATION: tc-DNA AON H51 (+68+82)

<400> SEQUENCE: 2
agaaatgcca tcttc                                                        15

<210> SEQ ID NO 3
<211> LENGTH: 15
<212> TYPE: DNA
<213> ORGANISM: Artificial Sequence
<220> FEATURE:
<223> OTHER INFORMATION: tc-DNA AON H51 (+70+84)

<400> SEQUENCE: 3
aaatgccatc ttcct                                                        15

<210> SEQ ID NO 4
<211> LENGTH: 15
<212> TYPE: DNA
<213> ORGANISM: Artificial Sequence
<220> FEATURE:
<223> OTHER INFORMATION: tc-DNA AON H51 (+73+87)

<400> SEQUENCE: 4
tgccatcttc cttga                                                        15

<210> SEQ ID NO 5
<211> LENGTH: 15
<212> TYPE: DNA
<213> ORGANISM: Artificial Sequence
<220> FEATURE:
<223> OTHER INFORMATION: tc-DNA AON SMN2i7 (10;25)

<400> SEQUENCE: 5
cuuucauaau gcugg                                                        15

<210> SEQ ID NO 6
<211> LENGTH: 13
<212> TYPE: DNA
<213> ORGANISM: Artificial Sequence
<220> FEATURE:
<223> OTHER INFORMATION: tc-DNA AON SMN2e7 (39;51)

<400> SEQUENCE: 6
uuaauuuaag gaa                                                          13

<210> SEQ ID NO 7
<211> LENGTH: 3
<212> TYPE: DNA
<213> ORGANISM: Artificial Sequence

```
<220> FEATURE:
<223> OTHER INFORMATION: tc-DNA AON DM1(CAGn)
<220> FEATURE:
<221> NAME/KEY: misc_feature
<222> LOCATION: (1)..(3)
<223> OTHER INFORMATION: (CAG)n : n repeat of (CAG) trinucleotide with
      n=4-7

<400> SEQUENCE: 7 cag                                                                        3

<210> SEQ ID NO 8
<211> LENGTH: 15
<212> TYPE: DNA
<213> ORGANISM: Artificial Sequence
<220> FEATURE:
<223> OTHER INFORMATION: tc-DNA AON DM1(CAG5)

<400> SEQUENCE: 8
cagcagcagc agcag                                                          15

<210> SEQ ID NO 9
<211> LENGTH: 21
<212> TYPE: DNA
<213> ORGANISM: Artificial Sequence
<220> FEATURE:
<223> OTHER INFORMATION: tc-DNA AON DM1(CAG7)

<400> SEQUENCE: 9
cagcagcagc agcagcagca g                                                   21

<210> SEQ ID NO 10
<211> LENGTH: 22
<212> TYPE: DNA
<213> ORGANISM: Mus musculus

<400> SEQUENCE: 10
tcaggtaagc cgaggtttgg cc                                                  22

<210> SEQ ID NO 11
<211> LENGTH: 17
<212> TYPE: DNA
<213> ORGANISM: Artificial Sequence
<220> FEATURE:
<223> OTHER INFORMATION: Tc-DNA AON SMN2e7(39;51)

<400> SEQUENCE: 11
uuaauuuaag gaaugug                                                        17

<210> SEQ ID NO 12
<211> LENGTH: 17
<212> TYPE: DNA
<213> ORGANISM: Artificial Sequence
<220> FEATURE:
<223> OTHER INFORMATION: Tc-DNA AON SMN2i7(10;25)

<400> SEQUENCE: 12
cacuuucaua augcugg                                                        17

<210> SEQ ID NO 13
<211> LENGTH: 22
<212> TYPE: DNA
<213> ORGANISM: Artificial Sequence
<220> FEATURE:
<223> OTHER INFORMATION: Ex 20 Fo Nested PCR primer

<400> SEQUENCE: 13
```
cagaattctg ccaattgctg ag                                                  22

<210> SEQ ID NO 14
<211> LENGTH: 20
<212> TYPE: DNA
<213> ORGANISM: Artificial Sequence
<220> FEATURE:
<223> OTHER INFORMATION: Ex 26 Ro Nested PCR primer

<400> SEQUENCE: 14
ttcttcagct tgtgtcatcc                                                     20

<210> SEQ ID NO 15
<211> LENGTH: 24
<212> TYPE: DNA
<213> ORGANISM: Artificial Sequence
<220> FEATURE:
<223> OTHER INFORMATION: Ex 20 Fi Nested PCR primer

<400> SEQUENCE: 15
cccagtctac caccctatca gagc                                                24

<210> SEQ ID NO 16
<211> LENGTH: 20
<212> TYPE: DNA
<213> ORGANISM: Artificial Sequence
<220> FEATURE:
<223> OTHER INFORMATION: Ex 26 Ri Nested PCR primer

<400> SEQUENCE: 16
cctgccttta aggcttcctt                                                     20

<210> SEQ ID NO 17
<211> LENGTH: 22
<212> TYPE: DNA
<213> ORGANISM: Artificial Sequence
<220> FEATURE:
<223> OTHER INFORMATION: Hex 49F2 Nested PCR primer

<400> SEQUENCE: 17
aaactgaaat agcagttcaa gc                                                  22

<210> SEQ ID NO 18
<211> LENGTH: 19
<212> TYPE: DNA
<213> ORGANISM: Artificial Sequence
<220> FEATURE:
<223> OTHER INFORMATION: Hex 53R2 Nested PCR primer

<400> SEQUENCE: 18
ttgcctccgg ttctgaagg                                                      19

<210> SEQ ID NO 19
<211> LENGTH: 21
<212> TYPE: DNA
<213> ORGANISM: Artificial Sequence
<220> FEATURE:
<223> OTHER INFORMATION: Hex 50F Nested PCR primer

<400> SEQUENCE: 19
aggaagttag aagatctgag c                                                   21

<210> SEQ ID NO 20
<211> LENGTH: 19
<212> TYPE: DNA

```
<213> ORGANISM: Artificial Sequence
<220> FEATURE:
<223> OTHER INFORMATION: Hex 52R2 Nested PCR primer

<400> SEQUENCE: 20
ttcttccaac tggggacgc                                             19

<210> SEQ ID NO 21
<211> LENGTH: 23
<212> TYPE: DNA
<213> ORGANISM: Artificial Sequence
<220> FEATURE:
<223> OTHER INFORMATION: SMN-Ex6-Fw PCR primer

<400> SEQUENCE: 21
gctgatgctt tgggaagtat gta                                        23

<210> SEQ ID NO 22
<211> LENGTH: 20
<212> TYPE: DNA
<213> ORGANISM: Artificial Sequence
<220> FEATURE:
<223> OTHER INFORMATION: SMN-Ex8-Re PCR primer

<400> SEQUENCE: 22
attccagatc tgtctgatcg                                            20
```

TRICYCLO-DNA ANTISENSE OLIGONUCLEOTIDES, COMPOSITIONS, AND METHODS FOR THE TREATMENT OF DISEASE

BACKGROUND OF THE DISCLOSURE

Technical Field

The present disclosure relates, generally, to synthetic antisense oligonucleotides (AON) and methods employing antisense oligonucleotides for modifying splicing events that occur during pre-mRNA processing or for down-regulating the expression of mutated mRNA that contain repeated sequences such as, for example, 3' or 5' CUG, CAG, and/or CCUG. More specifically, disclosed herein are tricyclo-DNA (tc-DNA) AON that are effective in facilitating exon skipping during pre-mRNA processing, in masking intronic silencer sequences and/or stem-loop sequences in pre-mRNA, and in targeting the RNase-mediated destruction of mRNA. Described herein are tc-DNA AON that may be used in methods for the treatment of Duchenne Muscular Dystrophy by skipping mutated exons, such as a mutated exon 23 or exon 51, within a dystrophin gene to restore functionality of a dystrophin protein. Also described are tc-DNA AON that may be used in methods for the treatment of Spinal Muscular Atrophy by masking an intronic silencing sequence and/or a terminal stem-loop sequence within an SMN2 gene to yield modified functional SMN2 protein, including an amino acid sequence encoded by exon 7, which is capable of at least partially complementing a non-functional SMN1 protein. Still further tc-DNA AON described herein may be used in methods for the treatment of Steinert's Myotonic Dystrophy by targeting the destruction of a mutated DM1 mRNA comprising 3'-terminal CUG repeats. Thus, tc-DNA AON and one or more of the foregoing approaches can be used to restore functionality in a protein involved in a myopathy.

Description of the Related Art

Duchenne Muscular Dystrophy (DMD) is the most common hereditary myopathy, afflicting about one in 3,500 males regardless of ethnicity. Although infrequent, girls and women may present Duchenne-like symptoms in manifesting carriers. The foremost consequence of DMD is that muscle fibers become particularly fragile and natural muscle activity provokes general damage in muscle tissue. The end-point observed in DMD, as well as in many muscle dystrophies, is that slow degeneration leads to almost complete fibrosis with fatty infiltration. Because of spine deformation and breathing difficulties, life expectancy in the 1960s was about 15 years. In the absence of cardiac complications, modern improvements in management methods (i.e. arthrodesis and tracheotomy ventilation) have increased life expectancy to 30 years.

Clinical symptoms of DMD are evident at the age of 18 months to three years and include a delayed ability to walk and climb, difficulty getting up from the floor, and abnormally enlarged calves. At about 5 to 6 years, muscle contractions develop in the foot, knee, and hip joints. Progression of the disease is characterized by a continual muscle wasting, leading at about 9 to 12 years to the loss of walking ability. In addition, some Duchenne boys present mental retardation suggesting that the missing protein is also involved in the central nervous system.

Duchenne Muscular Dystrophy is an X-linked recessive disorder. The DMD locus was identified on the X-chromosome (Xp21.2-OMIMid: 310200) in 1986, through a positional cloning approach, in a gene that encodes a protein called dystrophin. Mutations in the dystrophin gene result in a failure to produce dystrophin in striated muscles. Mothers of affected boys have a two-thirds chance of carrying a dystrophin mutation, while approximately one-third of patients have de novo mutations. More than half of DMD boys exhibit large genomic deletions encompassing one to several exons; few of them have large sequence duplications. Others have point mutations or very small deletions or duplications that are difficult to identify.

The extent of the mutations does not, however, directly correlate with the severity of the phenotype. Out-of-frame deletions or non-sense mutations that yield premature stop codons and subsequent abortion of translation result in dystrophin deficiencies characterized by severe phenotypes. In-frame deletions are responsible for a milder myopathy known as Becker muscular dystrophy (BMD).

With nearly 2.5 million base pairs, the DMD locus is the longest gene ever detected, but only about 14,000 base pairs contain coding sequences, which are spread over 79 exons. Full length dystrophin (DP 427) is a 427 kDa cytoskeletal protein expressed in all muscles, but a variety of protein isoforms (DP 260, DP 140, DP 116, DP 71) are generated by the tissue-specific, differential usage (in the retina, central nervous system, peripheral nervous system, and non-muscle tissues) of four internal promoters located in introns 29, 43, 55, and 62, respectively.

Full-length dystrophin is an essential component of a sarcolemmal glycoprotein complex (SGC) involved in sustaining the membrane integrity of muscle fibers by linking myofiber cytoskeleton to the extracellular matrix. Sequence analysis has predicted that the dystrophin protein entails several domains and repeats. Schematically, there is an actin-hybridizing site at the N-terminus (N-ABD); a central rod domain (RD; having 24 spectrin-like repeats) containing four hinge segments (H) that may confer flexibility; and a cystein-rich domain (CRD), which binds other members of the DPC, near the C-terminus (CT).

Structure/function analysis has identified domains which are crucial for protein function. This was exemplified by internal deletions occurring in some patients with a mild disease in whom the deletion encompassed exons 17 to 48 (46% of the coding sequence). England et al., Nature 343 (6254):180-2 (1990). This led to the concept of functional "minidystrophin" extensively used in the past 10 years in gene transfer experiments. It is now established that removal of the N-ABD and CT domains cause moderate loss of function, while the CRD is essential. Alterations of the RD result in diverse phenotypes depending on the extent and nature of the truncation. As an example, an RD deleted dystrophin (ΔR1-R24) is not functional, whereas a (ΔH2-R19) truncated dystrophin, which retains eight complete spectrin-like repeats out of 24, results in a protein with full activity.

There are two well-characterized genetic animal models for Duchenne Muscular Dystrophy. The mdx mouse harbors a non-sense mutation in exon 23 of the dystrophin gene, which precludes the synthesis of full-length, wild-type dystrophin protein. The mdx mouse displays a compensatory mechanism counteracting the degeneration, which could maintain the regeneration process to restore the mechanical damage. The mdx mouse does not exhibit symptoms of DMD and its life span is almost normal.

The GRMD (Golden Retriever Muscle Dystrophy) dog lacks functional dystrophin because of a splice site mutation in intron 6, which disrupts the reading frame. In GRMD, as with human DMD, the progressive degradation of fibers leads inexorably to skeletal musculature wasting with marked endomysial and perimysial fibrosis. Because of its DMD-like phenotype, GRMD remains the best available model for the evaluation of potential therapies for DMD.

Despite the identification and characterization of mutations in the dystrophin gene that are associated with an onset of DMD and the availability of suitable animal model systems for testing prospective therapeutic agents, there remains a need in the art for compositions and methods for the treatment of this disease. Several studies over the past 10 years support the benefit of steroid treatment (prednisone and deflazacort) in Duchenne boys, although a broad statistical evaluation has not yet been fully completed. Pharmacologic-induced read-through of premature stop-codon mutations by means of gentamicin medication could also potentially be effective in up to 5% of patients with DMD. Clinical trials are being carried out in the United States and Italy, even though the results of preclinical studies in the mdx mouse model were controversial. A new drug (PTC124) developed by PTC Therapeutics seems more promising. Studies are also underway to upregulate the utrophin gene using drugs whose product, the dystrophin-like protein utrophin, can compensate for the function of the missing dystrophin.

There are many other avenues of research; as an example, it has been recently shown that antagonizing myostatin by using blocking antibodies could improve muscle strength in mdx mice. This approach was initially based on multiple injections of normal myoblasts into the diseased muscles. Partridge et al., Nature 337(6203):176-9 (1989). Subsequent clinical trials (1991-98) have failed, although improving cell manufacturing and delivery procedures have made possible a new phase I trial in Canada (2002). Recent developments have also provided evidence that stem cells from either bone marrow or vascular origins can target skeletal muscle through the systemic pathway, even though the extent of the genetic correction is still insufficient.

Gene therapy for DMD lies on in situ delivery of dystrophin mini-genes into skeletal fibers by using gene vectors as vehicles. A first exploratory study using naked full length cDNA in a plasmid vector was carried out in France (2000-03). Among the different types of vectors that have been tested for muscle gene therapy, adenovirus associated virus (AAV)-derived vectors seem to be the most promising. AAV vectors have a number of advantages: (i) they are able to infect a wide variety of cell types including muscle fibers; (ii) they appear safe because they lack all viral genes and that wild type viruses have not yet been associated with any pathology in human; (iii) conversely to wild type AAVs, which integrate into the genome of the host cells, replication deficient AAV vectors generally persist as episomes thus limiting the risk of insertional mutagenesis or activation of oncogenes; and (iv) in contrast to other vector systems, AAV vectors do not trigger a significant immune response thus granting long term expression of the therapeutic transgenes (provided their gene products were not rejected). AAV vectors can also be produced at high titer and forced intra-arterial injections make them able to achieve gene transfer to significant muscle territories through a single injection, at least in rodents. Although AAV vectors lack all viral genes, their cargo shipment is limited to 4.5 kb. For that reason, the choice of AAV led to the development of μ-dystrophin variants of about 4 kb instead of the full-length dystrophin (14 kb). Several of these variants have been beneficially tested in the mdx model by either transgenesis or gene transfer.

In many DMD patients as well as in the mdx mouse and the GRMD dog, rare dystrophin-positive fibers have been reported. Although the proportion of revertant fibers increases with time, their number is unfortunately too low to confer a significant clinical benefit. The mechanism initiating these revertant fibers remains unknown although studies suggest that the reading-frame may be restored by exon-skipping. Such a natural phenomenon has prompted investigation into the design of strategies for gene repair/modulation based on the use of 2'-O-methyl antisense oligoribonucleotides as well as Morpholinos to interfere with splicing, thus inducing exon skipping. Indeed, this approach has been successfully used in vitro in mdx, GRMD and DMD muscle cells as well as in vivo (successful phase 1 clinical trial for 2'-O-methyl in Netherlands; a phase 1 with Morpholinos is ongoing in UK). Nevertheless, the weakness of this approach is that it requires regular administration of the synthetic AOs, and systemic delivery has not been fully achieved.

An alternative approach is to synthesize the sequences of interest in situ from vectors as antisense RNA molecules. Even so, producing "therapeutic" antisense RNA molecules in vivo poses many problems such as stability and subcellular localization. Small nuclear RNAs (snRNAs), which are known to participate in the splicing reaction, may be used as carriers to overcome these limitations. Recent reports have shown that U7 snRNA carrying antisense sequences against the splice junctions of either exon 23 or exon 51 of the dystrophin gene induce dystrophin synthesis in vitro as well as in vivo in mdx and Δ48-50 DMD cells, respectively.

An in silico search of all DMD patients with an out-of-frame deletion who would theoretically benefit from the skipping of a single exon adjacent to the deletion (on either side) has been performed. Interestingly, it is predicted that skipping exon 51 should restore a mini-dystrophin in 22% of the cases (i.e. Δ45-50, Δ47-50, Δ48-50, Δ49-50, Δ50 and Δ52). The resulting truncated proteins are expected to be at least partially functional since they correspond to deletions that have been found in some BMD patients. Additionally, a few healthy males carrying Δ51-52 and Δ48-51 in-frame deletions have been identified. Skipping of exon 51, in select patients, should bring about the production of a functional shorter dystrophin thus improving the phenotype.

Mental retardation is a symptom frequently associated with DMD and can result from the lack of dystrophin in neuronal cells. Rescuing a semi functional dystrophin in the brain could therefore correct or improve the cognitive impairment.

Spinal Muscular Atrophy (SMA) refers, generally, to a variety of disorders deriving from a common genetic defect in a survival motor neuron (SMN) gene, which, in 1990, was mapped to chromosome 5q11.2-13.3. Human chromosome 5 contains a large duplication such that there are two copies of the SMN gene, SMN1 and SMN2.

SMA is the most common cause of genetically determined neonatal death. All forms of SMN-associated SMA have a combined incidence of about 1 in 6,000. The gene frequency is around 1:80 and approximately one in 40 persons is a carrier. There are no known health consequences of being a carrier and the only way one may know to consider the possibility is if a relative is affected.

SMA is characterized by the loss of the motor neurons of the spinal cord and brainstem. In general, the earlier the symptoms appear, the shorter the expected life-span. Once symptoms appear, the motor neuron cells quickly deteriorate. All forms of SMA have in common weakness caused by denervation, that is, the muscle atrophies because it has lost the signal to contract due to loss of the innervating nerve. Spinal muscular atrophy only affects motor nerves. Heritable disorders that cause both weakness due to motor denervation along with sensory impairment due to sensory denervation are known by the inclusive label Charcot-Marie-Tooth or Hereditary Motor Sensory Neuropathy.

The course of SMA is directly related to the severity of weakness. Infants with the severe form of SMA frequently succumb to respiratory disease due to weakness of the muscles that support breathing. Children with milder forms of SMA naturally live much longer although they may need extensive medical support, especially those at the more severe end of the spectrum.

Type I SMA, also known as severe infantile SMA or Werdnig Hoffmann disease, is the most severe, and manifests in the first year of life. This type generally onsets quickly and unexpectedly after birth; babies diagnosed with Type I SMA do not generally live past one year of age. Pneumonia is considered the ultimate cause of death due to deterioration of survival motor neurons; motor neuron death causes insufficient functioning of the major bodily organ systems, particularly respiratory (e.g., breathing and ridding of pooled secretions inside lungs). Type II SMA, or intermediate SMA, describes those children who are never able to stand and walk, but who are able to maintain a sitting position at least some time in their life. The onset of weakness is usually recognized some time between 6 and 18 months. Weakness slowly and gradually increases over the life of the individual. Type III SMA patients are able to walk at some time.

SMA is typically diagnosed with a survival motor neuron (SMN) gene test, which determines whether there is at least one copy of a functional SMN1 gene, which is distinguished from the highly similar SMN2 gene, by the presence of exons 7 and 8 in fully-processed mRNA. The SMN2 gene also contains a mutation that makes it less efficient at making protein, though it does so in a low level. SMA is caused by loss of the SMN1 gene from both chromosomes and the inability of SMN2 protein to compensate for the loss in functional SMN1 protein.

Current strategies for developing SMA therapeutics include identifying drugs that increase SMN2 levels, enhance residual SMN2 function, or otherwise compensate for the loss of SMN1 activity. Drugs such as butyrates, valproic acid, hydroxyurea, and riluzole (Rilutek®, Sanofi Aventis) are or have been under clinical investigation for the treatment of SMA. Although gene replacement strategies are being tested in animals, current treatment for SMA consists of prevention and management of the secondary effect of chronic motor unit loss. There is currently no drug known to alter the course of SMA and it is likely that gene replacement for SMA will require many more years of investigation before it can be applied to humans.

Myotonic Dystrophy (DM) is a chronic, slowly progressing, highly variable inherited multisystemic disease that can manifest at any age from birth to old age. Myotonic dystrophy is the most common form of adult onset muscular dystrophy and the second most common form of any skeletal muscle disease after Duchenne muscular dystrophy. DM is characterized by wasting of the muscles (muscular dystrophy), posterior subcapsular iridescent cataracts (opacity of the lens of the eyes), heart conduction defects, endocrine changes and myotonia (difficulty relaxing a muscle).

There are currently two known types of adult onset DM, both identifiable by DNA analysis: Myotonic dystrophy type 1 (DM1) is commonly referred to as Steinert's disease, which has a congenital form that can severely affect babies and a childhood onset form. Myotonic dystrophy type 2 (DM2) is known as PROMM or proximal myotonic myopathy. Additional forms of myotonic dystrophy (e.g., DM3, DM4, DMX) are suspected, but their existence remains unproven. While both DM1 and DM2 are considered to be slowly degenerative conditions, DM2 is considered to be generally milder than DM1.

Presentation of symptoms varies considerably by form (DM1/DM2), severity and even unusual DM2 phenotypes. DM1 patients often present with myotonia, disabling distal weakness and severe cognitive problems. DM2 patients commonly present with muscle pain, stiffness, fatigue, or the development of proximal lower extremity weakness. Day et al. *Neurology* 60(4): 657-64 (2003). The characteristic pattern of weakness is different for DM1 and DM2. In DM1, it is noted in face and jaw muscles, the drooping of the eyelids (ptosis), weakness of the neck muscles, hands and lower legs. In DM2, the weakness is more evident in proximal muscles, those closer to the trunk of the body, neck, shoulders, hip flexors and upper legs.

DM1 symptoms include hypersomnia (daytime sleepiness), muscle wasting, dysphagia, and respiratory insufficiency. DM1 patients may experience a more diverse range of cognitive problems than DM2 patients. Depending on what form they have and the degree of severity, DM1 cognitive problems may range from developmental delays, learning problems, language, speech, behavior, apathy, or hypersomnia. Cognitive manifestations for DM2 include problems with executive function (i.e. organization, concentration, word-finding etc.) and hypersomnia.

In DM1, the affected gene is called DMPK (myotonic dystrophy protein kinase) and codes for a serine/threonine protein kinase expressed in skeletal muscle. The gene is located on the long arm of chromosome 19. In DM1, the DMPK gene is characterized by a triplet repeat of Cytosine-Thymine-Guanine (CTG). The number of repeats varies greatly from person to person, but the average number in a healthy person is between 5 and 37. Sometimes when repetitive sequences of DNA are repaired or replicated during cell division, the cellular machinery slips and an extra copy of the triplet repeat is added to the sequence. Once there are more than 37 triplet repeats in the DMPK gene the sequence becomes unstable and slippage becomes more common.

People affected with DM1 have over 50 and can have as many as 2000 CTG repeats. The result being that the repeat size of an individual with DM1 will become larger usually during gametogenesis or early embryonic development, such that children of an affected adult typically exhibit larger expansions than their parent due to slippage during gametogenesis (this phenomenon is referred to as anticipation). Individuals with larger expansions have an earlier onset of the disorder and a more severe phenotype.

DM2 is similarly caused by a defect of the ZNF9 gene on chromosome 3q21. The repeat expansion for DM2 is much larger than for DM1, ranging from 75 to over 11,000 repeats and involves a repeat of four nucleotides. Unlike DM1, however, the size of the repeated DNA expansion does not appear to make a difference in the age of onset or disease severity in DM2. Anticipation appears to be less significant in DM2.

There is currently no cure for or treatment specific to myotonic dystrophy. Heart problems, cataracts, and other abnormalities associated with the condition can be treated but not cured. There are, however, medical interventions and medications that may relieve some of the symptoms such as myotonia, pain, and excessive sleepiness. Research in areas such as high throughput screening and antisense therapy hold hope for more effective targeted treatments for the future. Altered splicing of the muscle-specific chloride channel 1 (ClC-1) causes the myotonic phenotype of DM1 and is reversible in mouse models using Morpholino antisense oligonucleotides that modify the splicing of ClC-1 mRNA. Wheeler et al., *J. Clin. Invest.* 117(12):3952-7 (2007).

Despite the ongoing search for therapeutic modalities for Duchenne Muscular Dystrophy, Spinal Muscular Atrophy, and Steinert's Myotonic Dystrophy, there remains an urgent need for efficacious compounds and therapeutic methods for the treatment of these diseases.

SUMMARY OF THE DISCLOSURE

The present disclosure fulfills these and other related needs by providing tricyclo-DNA (tc-DNA) antisense oligonucleotides (AON) and methods employing tc-DNA AON for the treatment of diseases such as Duchenne Muscular Dystrophy, Spinal Muscular Atrophy, and Steinert's Myotonic Dystrophy.

The invention also relates, generally, to a method of correcting abnormal gene expression in a cell of the central nervous system of a subject, the method comprising administering to the subject a tc-DNA antisense oligonucleotide, wherein said tc-DNA antisense oligonucleotide is complementary to a portion of an RNA encoded by said gene, and wherein said tc-DNA antisense oligonucleotide is administered peripherally to the subject in an amount sufficient to correct said abnotmal expression.

The invention also relates to a method of treating a genetic disease caused by abnormal gene expression in the central nervous system of a subject, the method comprising administering to the subject a tc-DNA antisense oligonucleotide, wherein said tc-DNA antisense oligonucleotide is complementary to a portion of an RNA encoded by said gene, and wherein said tc-DNA antisense oligonucleotide is administered peripherally to the subject in an amount effective to correct said abnormal expression.

The invention also relates to a pharmaceutical composition comprising a tc-DNA antisense oligonucleotide wherein said tc-DNA antisense oligonucleotide is complementary to a portion of an RNA encoded by a human gene, and wherein said composition further comprises a pharmaceutical acceptable excipient.

The invention also relates to a tc-DNA antisense oligonucleotide for use in the treatment of a genetic disease caused by abnormal gene expression in the central nervous system of a subject, said tc-DNA antisense oligonucleotide being complementary to a portion of an RNA encoded by said gene, and said tc-DNA antisense oligonucleotide being administered peripherally to the subject in an amount effective to correct said abnormal expression.

As used herein, the term "peripheral administration" includes, without limitation, any administration route which does not imply direct injection into the central nervous system of the subject in need of the treatment. More particularly, peripheral administration comprises systemic injections, such as intramuscular (i.m.), intravenous (i.v.), intraperitoneal (i.p.), intra-arterial, sub-cutaneous or transdermic injections.

The invention also relates to a tc-DNA antisense oligonucleotide for use in the treatment of a neuromuscular or musculo skeletal disease. The implemented tc-DNA antisense oligonucleotide is as herein described in further details below. More particularly, the tc-DNA antisense oligonucleotide may be one of the specific tc-DNA presented herein.

The neuromuscular or musculoskeletal disease can result from an alteration of a gene, wherein said alteration is an in-frame mutation of an exon, a mutation disrupting the translational reading frame of the gene, a deleterious mutation that can be compensated by the inclusion of an atypical exon in the mRNA coded by said gene, and the tc-DNA is complementary to an ISS or TSL present in a pre-mRNA coded by said gene and facilitates inclusion of an atypical exon, or a mutation resulting in the presence of deleterious 3' CUG amplification(s) in a mRNA coded by said gene.

In a particular embodiment, when the alteration is an in-frame mutation of an exon, said tc-DNA can facilitate skipping of said exon. In another embodiment, when the alteration is a mutation disrupting the translational reading frame of the gene, said tc-DNA can facilitate skipping of an exon so as to restore the reading frame of the gene. In another embodiment, when the alteration is a mutation resulting in the presence of deleterious 3' CUG amplification(s) in a mRNA coded by said gene and, said tc-DNA AON can destroy the mRNA containing said amplification.

The tc-DNA AON presented herein are constrained DNA AON that display improved hybridization properties with complementary pre-mRNAs as compared to DNA AON that employ, for example, more conventional 2'-O-methyl-phosphorothioate or Morpholino chemistries. While 2'-O-methyl-phosphorothioate or Morpholino DNA AON typically require 20 to 24 nucleotides to achieve specific pre-mRNA target hybridization, the presently disclosed tc-DNA AON are capable of specific pre-mRNA target hybridization with lengths of between 10 and 18 nucleotides, and more broadly between about 6 and about 22 nucleotides, in particular between 8 and 20 nucleotides.

As described in greater detail, below, exon skipping is achieved in the nucleus during the maturation process of pre-mRNAs. It includes the masking of key sequences involved in the splicing of targeted exons by using antisense oligonucleotides (AON) that are complementary to exon definition sequences within a pre-mRNA. Provided herein arc tc-DNA AONs that may be suitably employed for exon skipping through the masking of splice sites at intron/exon junctions, or more generally sites used for exon definition, within a dystrophin pre-mRNA thereby facilitating the deletion of a deleterious exon during the processing of the pre-mRNA to a mature mRNA. Such tc-DNA AON will find utility in the treatment of Duchenne Muscular Dystrophy by restoring an open reading frame in a mutated dystrophin gene comprising an exon that contains a non-sense, a stop, a frameshift mutation, or an intronic sequence that contains a deleterious cryptic exon.

For example, a non-sense or frameshift mutation within exon 23 or exon 51 of a dystrophin gene yields a carboxy-terminally truncated, non-functional dystrophin protein. By hybridizing to nucleotides comprising a dystrophin pre-mRNA splice donor site in intron 23 or intron 51, respectively, and adjacent 5' nucleotides of exon 23 or exon 51, tc-DNA AON disclosed herein are capable of preventing the inclusion of the mutated exon 23 or exon 51 into the mature mRNA transcript. The expression of that mature mRNA transcript yields a functional dystrophin protein that is deleted in the amino acids encoded by exon 23 or exon 51 but that includes dystrophin amino acids both N-terminal and C-terminal to those deleted amino acids and, therefore, constitutes a semi-functional 'quasi-dystrophin'.

The tc-DNA AONs disclosed herein for skipping an exon during processing of a dystrophin pre-mRNA contain between about 6 and about 22 nucleotides, in particular between about 8 and 20 tricyclo nucleotides, in particular between 10 and 18 tricyclo nucleotides, wherein 8-16 nucleotides of the tc-DNA AON are complementary to a dystrophin pre-mRNA intronic splice donor site, wherein 2-8 nucleotides of the tc-DNA AON are complementary to a dystrophin pre-mRNA exonic region, and wherein the intronic splice donor site is contiguous with and 5' to the exonic region. Within certain aspects, tc-DNA AONs are between 12 and 16 nucleotides or between 13 and 15 nucleotides and comprise between 6 and 14 nucleotides that are complementary to the intronic splice donor site and between 2 and 5 nucleotides that are complementary to the exonic region. It will be understood, however, that longer tc-DNA AON may be suitably employed to achieve exon skipping during processing of a dystrophin pre-mRNA.

Exemplified herein are tc-DNA AONs designed for skipping a mutated exon 23 within a dystrophin pre-mRNA. The tc-DNA AON comprise the nucleotide sequence 5'-AAC-CTCGGCTTACCT-3' (M23D (+02-13), SEQ ID NO: 1) and specifically hybridize to nucleotides at the 3' end of dystrophin pre-mRNA intron 23 and to nucleotides at the contiguous 5' end of dystrophin pre-mRNA exon 23. Also provided are tc-DNA AON designed for skipping a mutated exon 51 within a dystrophin pre-mRNA. The tc-DNA AON comprise a nucleotide sequence selected from the group consisting of 5'-AGAAATGCCATCTTC-3' (H51 (+68+82), SEQ ID NO: 2), 5'-AAATGCCATCTTCCT-3' (H51 (+70+84), SEQ ID NO: 3), and 5'-TGCCATCTTCCTTGA-3' (H51 (+73+87), SEQ ID NO: 4) and specifically hybridize to nucleotides at the 3' end of dystrophin pre-mRNA intron 51 and to nucleotides at the 5' end of dystrophin pre-mRNA exon 51.

The following nomenclature is used herein: "M" refers to mouse, "H" refers to human, "23" and "51" refer to specific exons, "D" refers to donor site, "A" refers to acceptor cite, "+" followed by a numeral indicates the number of nucleotides in the exon sequence, and "−" followed by a numeral indicates the number of nucleotides in the flanking exon. Thus, for example, M23D(+02-13) indicates that the tc-DNA AON encompasses the two 3'-terminal nucleotides of exon 23 and the 13 5'-terminal nucleotides of intron 23, which AON is capable of masking the donor splice site of mouse dystrophin exon 23 and H51(+68+82) indicates that the tc-DNA AON spans from nucleotide number 68 to nucleotide number 82 in human dystrophin exon 51.

Other aspects of the present disclosure provide tc-DNA AON that may be suitably employed for masking intronic silencing sequences (ISS) or terminal stem loops (TSL) within a survival motor neuron 2 (SMN2) pre-mRNA. Such tc-DNA AON facilitate the inclusion of an atypical exon during the processing of the SMN2 pre-mRNA to a mature mRNA. The resulting modified functional SMN2 protein contains the amino acid sequence encoded by the included atypical exon. Such a modified functional SMN2 protein is capable of complementing a non-functional SMN1 protein and, when expressed in vivo, can at least partially reverse Spinal Muscular Atrophy that is caused by mutations in the SMN1 gene.

For example, while exon 7 of SMN2 is typically excluded from the mature mRNA transcript through processing of the corresponding pre-mRNA, the addition of exon 7 yields a modified functional SMN2 protein that is capable of compensating functionally for the mutated SMN1 protein. By hybridizing to nucleotides comprising an SMN2 ISS or TSL within an SMN2 pre-mRNA, a tc-DNA AON can facilitate the inclusion of exon 7 into the mature mRNA transcript. The expression of that mature mRNA transcript yields a modified functional SMN2 protein that includes the amino acids encoded by exon 7 as well as all other SMN2 amino acids both N-terminal and C-terminal to those included amino acids.

Thus, the present disclosure provides tc-DNA AON for facilitating the inclusion of exon 7 during processing of the SMN2 pre-mRNA wherein the tc-DNA AON is 6-22 tricyclo nucleotides in length, in particular between 8-20 tricyclo nucleotides, more particularly between 10-18 tricyclo nucleotides in length and wherein the tc-DNA AON is complementary to an SMN2 pre-mRNA intronic silencer sequence (ISS) or a terminal stem-loop (TSL). Such tc-DNA AON may be between 13 and 17 nucleotides, between 12 and 16 nucleotides, or between 13 and 15 nucleotides. Exemplified herein are tc-DNA AON that comprise the 15-nucleotide sequence 5'-CUUUCAUAAUGCUGG-3' (SMN2i7(10;25), SEQ ID NO: 5), which tc-DNA AON are complementary to an SMN2 pre-mRNA ISS and which may be employed to facilitate the inclusion of exon 7 into a processed SMN2 mRNA. Also exemplified herein are tc-DNA AON that comprise the 13-nucleotide sequence 5'-UUAAUUUAAGGAA-3' (SMN2e7(39;51), SEQ ID NO: 6), which tc-DNA AON are complementary to an SMN2 pre-mRNA TSL2 and which may also be employed to facilitate the inclusion of exon 7 into a processed SMN2 mRNA. It will be understood that combinations of the tc-DNA AON presented herein may also be employed Still further aspects of the present disclosure provide tc-DNA AON that may be suitably employed for facilitating the destruction of a mutated DM1 mRNA. Such tc-DNA AON comprise 9-27 tricyclo nucleotides, wherein the tc-DNA AON is complementary to a mutated DM1 mRNA comprising deleterious 3' CUG amplification(s) (n>50) and wherein the tc-DNA AON is capable of facilitating the RNase-mediated destruction of said DM1 mRNA. Tc-DNA AON may comprise between 3 and 9; between 4 and 8; or 5, 6, or 7 contiguous repeats of the nucleotide sequence 5'-CAG-3' (SEQ ID NO: 7). An exemplary tc-DNA AON for facilitating the destruction of a mutated DM1 comprises the 15-nucleotide sequence 5'-CAGCAGCAGCAGCAG-3' (DM1(CAG5), SEQ ID NO: 8). Another exemplary tc-DNA AON facilitating the destruction of a mutated DM1 comprises the 21-nucleotide sequence 5'-CAGCAGCAGCA-GCAGCAGCAG-3' (DM1(CAG7), SEQ ID NO: 9).

In other aspects, the present disclosure provides methods for eliminating a mutated exon from a dystrophin mRNA, methods for including an atypical exon within an SMN2 mRNA, and methods for destroying a DM1 mRNA comprising a pathological number of 3' CUG amplifications in a cell. Each of these methods includes the step of contacting a cell with a tc-DNA AON as disclosed herein.

Within certain embodiments are provided methods for eliminating a mutated exon from a dystrophin mRNA, which methods comprise the step of contacting a cell that expresses a dystrophin pre-mRNA with a tc-DNA AON containing between 6-22 tricyclo nucleotides in length, in particular between 8-20 tricyclo nucleotides, more particularly between 10 and 18 tricyclo nucleotides, wherein 8-16 nucleotides of the tc-DNA AON are complementary to a dystrophin pre-mRNA intronic splice donor site, wherein 2-8 nucleotides of the tc-DNA AON are complementary to a dystrophin pre-mRNA exonic region, and wherein the exonic region is contiguous with and 3' to the intronic splice donor site. Exemplary methods include the step of contacting the cell with a tc-DNA AON of between 12 and 16 nucleotides or between 13 and 15 nucleotides. Suitable tc-DNA AON for use in such methods comprise the nucleotide sequence 5'-AACCTCGGCTTACCT-3' (M23D (+02-

13), SEQ ID NO: 1); 5'-AGAAATGCCATCTTC-3' (H51 (+68+82), SEQ ID NO: 2), 5'-AAATGCCATCTTCCT-3' (H51 (+70+84), SEQ ID NO: 3), and 5'-TGCCATCTTCCT-TGA-3' (H51 (+73+87), SEQ ID NO: 4).

Within other embodiments are provided methods for including an atypical exon within an SMN2 mRNA, which methods comprise the step of contacting a cell that is expressing an SMN2 pre-mRNA with a tc-DNA AON that contains between 6-22 tricyclo nucleotides in length, in particular between 8-20 tricyclo nucleotides, more particularly between 10 and 18 or between 11 and 18 tricyclo nucleotides, wherein the tc-DNA AON is complementary to an SMN2 pre-mRNA intronic silencer sequence (ISS), such as ISS-N1 within intron 7. Exemplary methods include the step of contacting the cell with a tc-DNA AON of between 12 and 16 nucleotides or between 13 and 15 nucleotides. Suitable tc-DNA AON for use in such methods comprise the 15-nucleotide sequence 5'-CUUUCAUAAUGCUGG-3' (SIV1N2i7(10;25), SEQ ID NO: 5). Within related methods, the tc-DNA AON is complementary to an SMN2 pre-mRNA terminal stem-loop (TSL), such as TSL-2 within exon 7. Suitable tc-DNA AON for use in such methods comprise the 13-nucleotide sequence 5'-UUAAUUUAAGGAA-3' (SMN2e7(39;51), SEQ ID NO: 6).

Within still further embodiments are provided methods for destroying a DM1 mRNA comprising one or more 3' CUG amplifications in a cell, which methods comprise the step of contacting a cell with a tc-DNA AON comprising 9-27 tricyclo nucleotides wherein the tc-DNA AON is complementary to a mutated DM1 mRNA comprising one or more 3' CUG amplification(s) and wherein the tc-DNA AON is capable of facilitating the RNase-mediated destruction of the DM1 mRNA. Suitable tc-DNA AON for use in such methods comprise between 3 and 9; between 4 and 8; or 5, 6, or 7 contiguous repeats of the nucleotide sequence 5'-CAG-3' (SEQ ID NO: 7) and are exemplified by tc-DNA AON comprising the 15-nucleotide sequence 5'-CAGCA-GCAGCAGCAG-3' (DM1(CAG5), SEQ ID NO: 8). Another exemplary tc-DNA AON facilitating the destruction of a mutated DM1 comprises the 21-nucleotide sequence 5'-CAGCAGCAGCAGCAGCAGCAG-3' (DM1(CAG7), SEQ ID NO: 9).

In other aspects, the present disclosure provides methods for the treatment of Duchenne Muscular Dystrophy (DMD), methods for the treatment of Spinal Muscular Atrophy (SMA), and methods for the treatment of Steinert's Myotonic Dystrophy (SD). Each of these methods employ the step of administering to a patient a tc-DNA AON, as disclosed herein, for eliminating a mutated exon from a dystrophin mRNA, for including an atypical exon within an SMN2 mRNA, or for destroying a DM1 mRNA comprising one or more 3' CUG amplifications, respectively.

These and other embodiments, features and advantages of the disclosure will become apparent from the detailed description and the appended claims set forth herein below.

BRIEF DESCRIPTION OF THE DRAWINGS

FIGS. 10A-C are sections at the level of the hippocampus of normal, mdx and treated mdx with 20 µg tc-DNA M23D (+02-13), one month after a single intrathecal injection. FIGS. 10D-F are sections at the level of the cerebellum of normal, mdx and treated mdx with 200 µg tc-DNA M23D (+02-13), one month after delivery in the cerebrospinal fluid. Nuclei are counterstained with DAPI.

DETAILED DESCRIPTION

Figure 1:
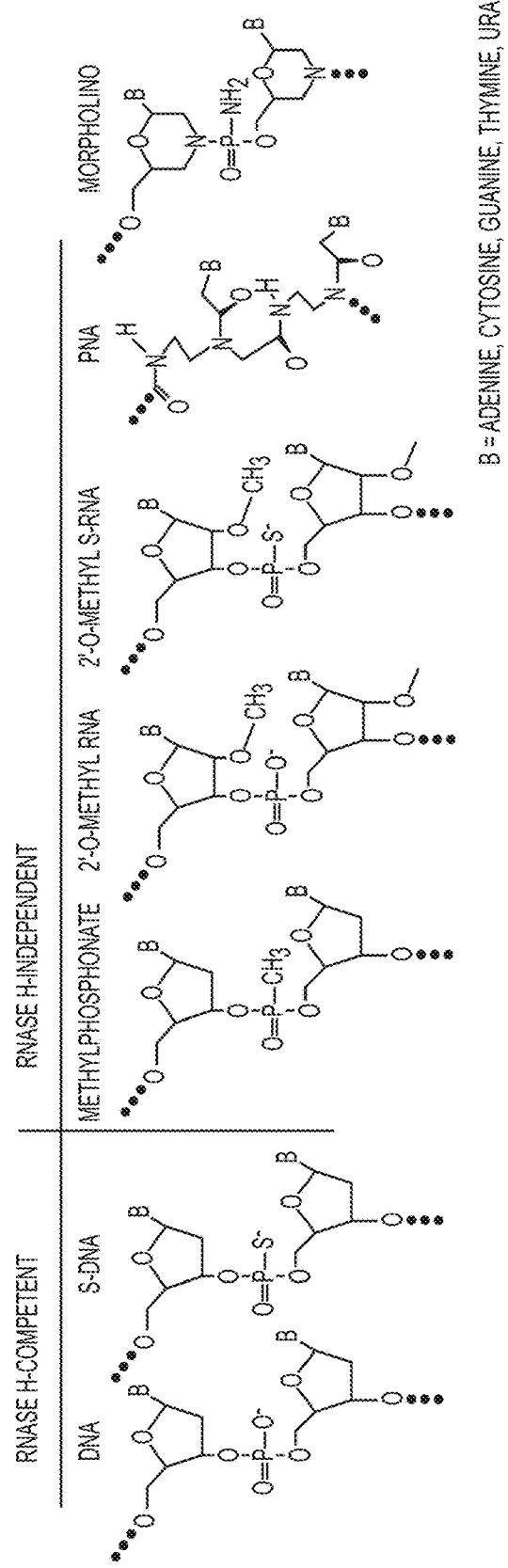
FIG. 1 is a table of various synthetic nucleotides used for the production of antisense oligonucleotides.
Figure 2:
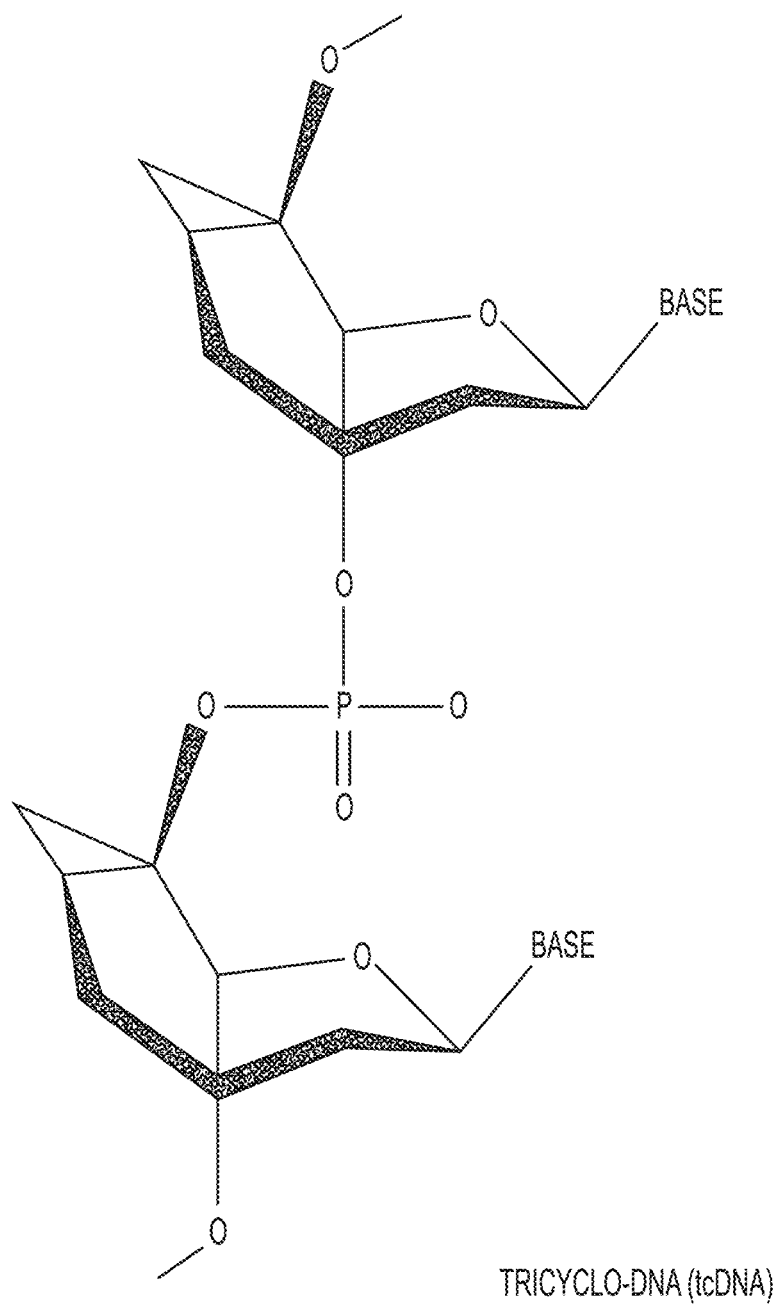
FIG. 2 is a structural representation of a tricyclo-DNA (tc-DNA).

The present disclosure is based upon the unexpected discovery that tricyclo-DNA (tc-NA) antisense oligonucleotides (AON) may be suitably employed for masking pre-mRNA splice sites within the dystrophin gene, for masking intronic silencing sequences or terminal stem-loop sequences within an SMN2 gene, or for destroying a DM1 mRNA comprising one or more 3' CUG amplifications. These discoveries will find broad application in the treatment of genetic diseases, generally, and, more specifically, in the treatment of Duchenne Muscular Dystrophy, Spinal Muscular Atrophy, and Steinert's Myotonic Dystrophy.

Tricyclo-DNA (tc-DNA) belongs to a new class of constrained DNA analogs that display improved hybridizing capacities to complementary RNA. Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova et al., *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., *JACS.* 124:5993-6002 (2002). Pre-mRNA/tc-DNA AON heteroduplexes disclosed herein are resistant to RNase H and, as a consequence, prevent the destruction of the targeted pre-mRNA. The advantage of the tricyclo-DNA chemistry is that the structural properties of its backbone allow a reduction in the length of an AON while retaining high affinity and highly specific hybridization with a complementary nucleotide sequence. Unexpectedly, tc-DNA AON may be advantageously used in microgram dosages in the in vivo setting using intramuscular application, which are at least 10-fold less than the dosages required for conventional antisense oligonucleotide technologies. In addition, tc-DNA retain full activity with reduced antisense lengths. Thus, for example, tc-DNA AON of 13 to 15 nucleotides are highly effective in the ex vivo and in vivo applications exemplified by the present disclosure.

The tc-DNA AON described herein also exhibit increased in vivo stability as compared to existing antisense oligonucleotide chemistries such as, for example, 2'-O-methyl-phosphorothioate or Morpholino chemistries. Thus, for example, a single intramuscular injection of a tc-DNA AON of the present disclosure retains in vivo efficacy for more than 20 weeks following administration.

Furthermore, and quite surprisingly, tc-DNA AON of the present disclosure, as exemplified by the tc-DNA AON designated M23D(+02-13), can be delivered into the central nervous system (CNS), either through intra-parenchymal or intra-ventricular administration or by administration into the subarachnoid space, to restore within the neurons of the hippocampus CA1 or within neurons of the cerebral or the cerebellar cortex, a mutated gene, such as a mutated dystrophin gene. Thus, it is demonstrated that tc-DNA AON described herein can efficiently cross the ependymal barrier.

The present disclosure will be best understood by reference to the following definitions:

Definitions

As used herein, the term "tricyclo-DNA (tc-DNA)" refers to a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs.

As used herein, the term "antisense oligonucleotide (AON)" refers to an oligonucleotide that is capable of interacting with and/or hybridizing to a pre-mRNA or an mRNA having a complementary nucleotide sequence thereby modifying gene expression. Enzyme-dependent anti sense oligonucleotides include forms that are dependent on RNase H activity to degrade target mRNA, and include single-stranded DNA, RNA, and phosphorothioate antisense. Steric blocking antisense oligonucleotides (RNase-H independent antisense) interfere with gene expression or other mRNA-dependent cellular processes by binding to a target sequence of mRNA. Steric blocking antisense includes 2'-O alkyl antisense oligonucleotides, Morpholino antisense oligonucleotides, and tricyclo-DNA antisense oligonucleotides. As described herein, within certain applications tc-DNA antisense oligonucleotides may be employed in enzyme-dependent applications such as, for example, the RNase-mediated destruction of DM1 mRNA comprising one or more 3' CUG amplifications.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the tc-DNA AON of the present disclosure, the binding free energy for a tc-DNA AON with its complementary sequence is sufficient to allow the relevant function of the tc-DNA AON to proceed and there is a sufficient degree of complementarity to avoid non-specific binding of the tc-DNA AON to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et al., *CSH Symp. Quant. Biol. LII*:123-133 (1987); Frier et al., *Proc. Nat. Acad. Sci. USA* 83:9373-77 (1986); and Turner et al., *J. Am. Chem. Soc.* 109:3783-3785 (1987)). Thus, "complementary" (or "specifically hybridizable") are terms that indicate a sufficient degree of complementarity or precise pairing such that stable and specific binding occurs between a tc-DNA AON and a pre-mRNA or mRNA target.

It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is comprised exclusively of exons. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

Figure 11:
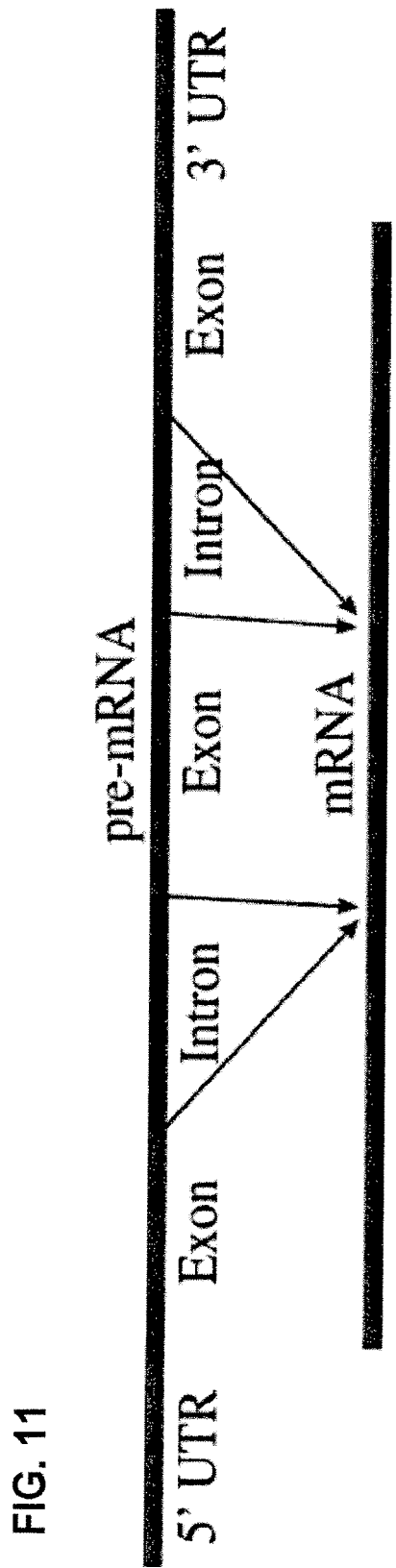
FIG. 11 is a diagrammatic representation of the overall processing of pre-mRNA into a mature mRNA.

As used herein, the terms "splicing" and "processing" refers to the modification of a pre-mRNA following transcription, in which introns are removed and exons are joined. (See, FIG. 11). Splicing occurs in a series of reactions that are catalyzed by a large RNA-protein complex composed of five small nuclear ribonucleoproteins (snRNPs) referred to as a spliceosome. Within an intron, a 3' splice site, a 5' splice site, and a branch site are required for splicing. The RNA components of snRNPs interact with the intron and may be involved in catalysis.

Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS) and terminal stem loop (TSL) sequences.

As used herein, the terms "intronic silencer sequences (ISS)" and "terminal stem loop (TSL)" refer to sequence elements within introns and exons, respectively, that control alternative splicing by the binding of trans-acting protein factors within a pre-mRNA thereby resulting in differential use of splice sites. Typically, intronic silencer sequences are between 8 and 16 nucleotides and are less conserved than the splice sites at exon-intron junctions. Terminal stem loop sequences are typically between 12 and 24 nucleotides and form a secondary loop structure due to the complementarity, and hence binding, within the 12-24 nucleotide sequence.

As used herein, the term "Spinal Muscular Atrophy (SMA)" refers to different clinical types of chromosome 5-linked SMA, each having in common a genetic cause and the manifestation of weakness due to loss of the motor neurons of the spinal cord and brainstem. Spinal Muscular Atrophy is caused by mutations within the survival motor neuron gene SMN1. At least one normal allele of the SMN1 gene is required for normal function.

The region of chromosome 5 that contains the SMN (survival motor neuron) gene has a large duplication. A large sequence that contains several genes occurs twice in adjacent segments. There are thus two copies of the gene, SMN1 and SMN2. The SMN2 gene has an additional mutation that makes it less efficient at making protein, though it does so in a low level. SMA is caused by loss of the SMN1 gene from both chromosomes. The severity of SMA, ranging from SMA 1 to SMA 3, is partly related to how well the remaining SMN 2 genes can make up for the loss of SMN 1. Often there are additional copies of SMN2, and an increasing number of SMN2 copies are related to less severe disease.

By "subject" is meant an organism, which is a donor or recipient of explanted cells or the cells themselves. "Subject" also refers to an organism to which the nucleic acid molecules of this disclosure can be administered. In one embodiment, a subject is a mammal or mammalian cell. In another embodiment, a subject is a human or human cell.

As used herein, the term "therapeutically effective amount" means an amount of tc-DNA AON that is sufficient, in the subject (e.g., human) to which it is administered, to treat or prevent the stated disease, disorder, or condition. The tc-DNA AON of the instant disclosure, individually, or in combination or in conjunction with other drugs, can be used to treat diseases or conditions discussed herein. For example, to treat a particular disease, disorder, or condition, the tc-DNA AON can be administered to a patient or can be administered to other appropriate cells evident to those skilled in the art, individually or in combination with one or more drugs, under conditions suitable for treatment.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "isolated" means that the referenced material is removed from its native environment, e.g., a cell. Thus, an isolated biological material can be free of some or all cellular components, i.e. components of the cells in which the native material occurs naturally (e.g., cytoplasmic or membrane component).

The term "purified" as used herein refers to material that has been isolated under conditions that reduce or eliminate the presence of unrelated materials, i.e. contaminants, including native materials from which the material is obtained. For example, a purified tc-DNA AON is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean ±20% of the indicated range, value, or structure, unless otherwise indicated.

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Tricyclo-DNA Antisense Oligonucleotides for the Treatment of Duchenne Muscular Dystrophy As indicated above, within certain embodiments, the present disclosure provides tc-DNA AON that may be suitably employed for the treatment of Duchenne Muscular Dystrophy (DMD), a severe recessive x-linked form of muscular dystrophy that is characterized by rapid progression of muscle degeneration, eventually leading to loss in ambulation, paralysis, and death. DMD is caused by a mutation, such as a non-sense or frame-shift mutation, within a dystrophin gene, which is located on the human X chromosome. The dystrophin gene encodes the dystrophin protein, an important structural component within muscle tissue which provides structural stability to muscle fibre sarcolemma as well as to the dystroglycan complex (DGC), located at the cell membrane. A non-sense or frame-shift mutation results in premature termination of translation and, hence, a C-terminally truncated dystrophin protein.

DMD caused by one or more stop mutation(s) or frame-shift mutation(s) can be relieved by excising one or several exons so as to restore the translational reading frame and thereby restoring the mRNA sequence downstream of the mutation. To achieve this, as part of the present disclosure, tc-DNA AON were developed to target regions within the pre-mRNA that can mask spliceosomal recognition of one or more exon(s). By targeting these regions with tc-DNA AON exons may be removed via alternative splicing to yield mature, functional dystrophin mRNA.

Thus, the tc-DNA AON described herein are effective in facilitating the skipping of one or more mutated exons in a dystrophin gene during the processing of a dystrophin pre-mRNA thereby restoring the proper reading frame of the resulting dystrophin mRNA, which, when translated, yields a functional dystrophin protein. Thus, the tc-DNA AON disclosed herein may be used therapeutically for patients afflicted with DMD.

As used herein, the term "exon skipping" refers to the modification of pre-mRNA splicing by the targeting of splice donor and/or acceptor sites within a pre-mRNA with one or more complementary antisense oligonucleotide(s) (AONs). By blocking access of a spliceosome to one or more splice donor or acceptor site, an AON can prevent a splicing reaction thereby causing the deletion of one or more exons from a fully-processed mRNA. Exon skipping is achieved in the nucleus during the maturation process of pre-mRNAs. It includes the masking of key sequences involved in the splicing of targeted exons by using antisense oligonucleotides (AON) that are complementary to splice donor sequences within a pre-mRNA. The tc-DNA AON provided herein may be suitably employed for exon skipping through the masking of splice sites at intron/exon junctions within a dystrophin pre-mRNA thereby facilitating the deletion of a mutant exon during the processing of the pre-mRNA to a mature mRNA.

For example, a non-sense or frameshift mutation within exon 23 or exon 50 of a dystrophin gene yields a carboxy-terminally truncated, non-functional dystrophin protein. By hybridizing to nucleotides comprising a dystrophin pre-mRNA splice donor site in intron 23 or intron 51, respectively, and adjacent 5' nucleotides of exon 23 or exon 51, tc-DNA AON disclosed herein are capable of preventing the inclusion of the mutated exon 23 or exon 51 into the mature mRNA transcript. The expression of that mature mRNA transcript yields a functional dystrophin protein that is deleted in the amino acids encoded by exon 23 or exons 50 and 51 but that includes dystrophin amino acids both N-terminal and C-terminal to those deleted amino acids.

The tc-DNA AON disclosed herein for skipping an exon during processing of a dystrophin pre-mRNA typically contain between 6-22 contiguous tricyclo nucleotides, in particular between 8-20 tricyclo nucleotides, more particularly between 10 and 18 contiguous tricyclo nucicotidcs, wherein 6-16 nucicotidcs, in particular 8-16 nucicotidcs of the tc-DNA AON arc complementary to a dystrophin pre-mRNA intronic splice donor site, wherein 2-8 nucleotides of the tc-DNA AON are complementary to a dystrophin pre-mRNA exonic region, and wherein the intronic splice donor site is contiguous with and 5' to the exonic region. Depending upon the precise application contemplated, tc-DNA AON may be between 12 and 16 nucleotides or between 13 and 15 nucleotides and may comprise between 6 and 14 nucleotides that are complementary to the intronic splice donor site and between 2 and 5 nucleotides that are complementary to the exonic region.

Exemplified herein are tc-DNA AON designed for skipping a mutated exon 23 within a dystrophin pre-mRNA. The tc-DNA AON comprise the nucleotide sequence 5'-AAC-CTCGGCTTACCT-3' (M23D (+02-13), SEQ ID NO: 1) and specifically hybridize to nucleotides at the 3' end of dystrophin pre-mRNA intron 23 and to nucleotides at the contiguous 5' end of dystrophin pre-mRNA exon 23. Also provided are tc-DNA AON designed for skipping a mutated exon 51 within a dystrophin pre-mRNA. The tc-DNA AON comprise a nucleotide sequence selected from the group consisting of 5'-AGAAATGCCATCTTC-3' (H51 (+68+82), SEQ ID NO: 2), 5'-AAATGCCATCTTCCT-3' (H51 (+70+84), SEQ ID NO: 3), and 5'-TGCCATCTTCCTTGA-3' (H51 (+73+87), SEQ ID NO: 4) and specifically hybridize to nucleotides at the 3' end of dystrophin pre-mRNA intron 51 and to nucleotides at the 5' end of dystrophin pre-mRNA exon 51.

Tricyclo-DNA Antisense Oligonucleotides for the Treatment of Spinal Muscular Atrophy Within other embodiments, the present disclosure provides tc-DNA AON that may be suitably employed for the treatment of Spinal Muscular Atrophy (SMA). SMA is caused by mutations in both copies of the SMN1 gene, which in a normal cell is characterized by the presence of exons 7 and 8 in fully-processed mRNA. Because normally processed SMN2 mRNA does not contain exons 7 or 8, the SMN2 protein cannot compensate for a loss in the functional SMN1 protein. By masking an intronic silencing sequence (ISS) and/or a terminal stem loop (TSL) within an SMN2 pre-mRNA, tc-DNA AON described herein are capable of facilitating the inclusion of atypical exon 7 or exon 8 into a processed SMN2 pre-mRNA, which is translated into a modified functional SMN2 protein that is capable of compensating for the loss of functional SMN1 protein and, when expressed in vivo, the modified functional SMN2 can at least partially reverse Spinal Muscular Atrophy that is caused by a mutation in the SMN1 gene.

Thus, the present disclosure provides tc-DNA AON for facilitating the inclusion of an atypical exon during processing of an SMN2 pre-mRNA wherein the tc-DNA AON is 6-22 tricyclo nucleotides in length, in particular between 8-20 tricyclo nucleotides, more particularly between 10-18 tricyclo nucleotides in length and wherein the tc-DNA AON is complementary to an SMN2 pre-mRNA intronic silencer sequence (ISS) or a terminal stem-loop (TSL). Such tc-DNA AON may be between 13 and 17 nucleotides, between 12 and 16 nucleotides, or between 13 and 15 nucleotides.

Exemplified herein are tc-DNA AON that comprise the 15-nucleotide sequence 5'-CUUUCAUAAUGCUGG-3' (SMN2i7(10;25), SEQ ID NO: 5), which tc-DNA AON are complementary to an SMN2 pre-mRNA ISS and which may be employed to facilitate the inclusion of atypical exon 7 into a processed SMN2 mRNA. Also exemplified herein are tc-DNA AON that comprise the 13-nucleotide sequence 5'-UUAAUUUAAGGAA-3' (SMN2e7(39;51), SEQ ID NO: 6), which tc-DNA AON are complementary to an SMN2 pre-mRNA TSL2 and which may also be employed to facilitate the inclusion of exon 7 into a processed SMN2 mRNA.

Tricyclo-DNA Antisense Oligonucleotides for the Treatment of Steinert's Myotonic Dystrophy Within still further embodiments, the present disclosure provides tc-DNA AON that may be suitably employed for the treatment of Steinert's Myotonic Dystrophy that results from CUG amplifications at the 3' end of the mRNA encoding DM1. It is believed that mutated DM1 mRNAs that contain excessive CUG amplifications are sequestered into the nucleus and accumulate to form nuclear foci. These foci are stable and are thought to bind to factors involved in the splicing machinery thereby widely affecting the transcriptome. As part of the present disclosure, it is demonstrated, by using a U7 snRNA system, that tc-DNA AON may be employed to target the CUG sequences and facilitate the destruction of the mutated DM1 mRNA thereby leading to the release of the splicing factors and removal of the nuclear foci. Without being bound to a particular mechanistic theory, it is further believed, quite surprisingly, that the tc-DNA AON disclosed herein are capable of facilitating destruction of mRNA containing excessive CUG amplifications.

Thus, tc-DNA AON are described that may be suitably employed for facilitating the destruction of a mutated DM1 mRNA comprising excess CUG amplifications. Such tc-DNA AON comprise 9-27 tricyclo nucleotides, wherein the tc-DNA AON is complementary to a mutated DM1 mRNA comprising one or more 3' CUG amplification(s) and wherein the tc-DNA AON is capable of facilitating the destruction of the DM1 mRNA. Depending upon the precise application contemplated, tc-DNA AON may comprise between 3 and 9; between 4 and 8; or 5, 6, or 7 contiguous repeats of the nucleotide sequence 5'-CAG-3' (SEQ ID NO: 7). An exemplary tc-DNA AON for facilitating the destruction of a mutated DM1 comprises the 15-nucleotide sequence 5'-CAGCAGCAGCAGCAG-3' (DM1(CAG5), SEQ ID NO: 8). Another exemplary tc-DNA AON facilitating the destruction of a mutated DM1 comprises the 15-nucleotide sequence 5'-CAGCAGCAGCAGCAGCAGCAG-3' (DM1(CAG7), SEQ ID NO: 9).

Synthesis and Isolation of Tricyclo-DNA Antisense Oligonucleotides

Tc-DNA AON may be synthesized using protocols known in the art, for example as described in Caruthers et al., *Methods in Enzymol.* 211:3-19 (1992); Thompson et al., PCT Publication No. WO 99/54459; Wincott et al., *Nucleic Acids Res.* 23:2677-2684 (1995); Wincott et al., *Methods Mol. Bio.* 74:59 (1997); Brennan et al., *Biotechnol Bioeng.* 61:33-45 (1998); and Brennan, U.S. Pat. No. 6,001,311.

Methodologies for the synthesis of tc-DNA and tc-DNA AON have been described and are well known in the art. See, for example, Steffens and Leumann, *J. Am. Chem. Soc.* 121(14):3249-3255 (1999); Steffens and Leumann, *J.Am.Chem.Soc.* 119:11548-11549 (1997); and Wengel, U.S. Pat. No. 7,034,133. Tc-DNA may be synthesized on a commercial DNA synthesizer from phosphoramidites generated by conventional solid-phase cyanoethyl phosphoramidite chemistry. The tc-DNA phosphoramidite building blocks may be synthesized as described in Steffens and Leumann, *C. Helv. Chim. Acta* 80:2426-2439 (1997). Chain-extension cycles may be essentially identical to those for natural oligodeoxynucleotide synthesis. See, Pharmacia LKB User's Manual (56-1111-56) (Gene Assembler Special/4 Primers).

For example, synthesis of tc-DNA AON may be achieved by the solid-phase phosphoramidite methodology using a Pharmacia LKS Gene Assembler Special instrument or an Applied Biosystems PCR-MATE EP DNA Synthesizer (Model 391) connected to a personal computer. Reagent solutions may be prepared according to the manufacturer's protocols. See, User's Manual, Applied Biosystems PCR_MATE EP DNA Synthesizer (Model 391 (1989) and Pharmacia LKB User's Manual (56-1111-56) (Gene Assembler Special/4 Primers). 1H-tetrazole (0.45 M solution in MeCN) may be obtained from Fluka.

The assembly of tricyclo-DNA AON may be performed according to the standard synthesis cycles with the exception that a prolonged coupling time (e.g., 6 minutes), an 11-fold excess of phosphoramidites, and the use of a 0.07 M instead of a 0.1 M solution of tricycloadenosine building block may be employed due to its poor solubility. Either LCAA-CPG (Sigma) or polystyrene (Pharmacia) bound natural nucleosides may be used as starter units.

Synthesis may be performed in the trityl off mode, ending with 5'-detritylated oligomers. Coupling efficiencies may be monitored by on-line trityl assay and are typically between 90 and 99%. After synthesis, the solid support may be suspended in concentrated $NH_3$ solution and left for 15 hours at 55° C. or 2 hours at room temperature.

Crude tc-DNA AON may be purified by any of a number of methodologies known in the art such as, for example, ultrafiltration, gel electrophoresis, or chromatography. Ion-exchange HPLC may be achieved on a Nucleogen DEAE 60-7 (125×4 mm) column. The isolated oligonucleotides may be desalted over a SP-PAK C-18 cartridge (Waters) as described in Sambrook et al., "Molecular Cloning: A Laboratory Manual" 11.29 (Cold Spring Harbor Laboratory Press, Plainview, N.Y., 1989). The purified tc-DNA AON may be dissolved in 150 mM NaCl, 10 mM Tris-HCl, pH 7.0 and incubated with alkaline phosphatase (1 mg/ml) and phosphodiesterase (2 mg/ml) at 37° C. After 5 hours, the solution may be subjected to HPLC purification.

Chemically synthesizing nucleic acid molecules with substitutions or modifications (base, sugar or phosphate) can prevent their degradation by serum ribonucleases, which can increase their potency. See, e.g., Eckstein et al., PCT Publication No. WO 92/07065; Perrault et al., *Nature* 344:565 (1990); Pieken et al., *Science* 253:314 (1991); Usman and Cedergren, *Trends in Biochem. Sci.* 17:334 (1992); Usman et al., PCT Publication No. WO 93/15187; and Rossi et al., PCT Publication No. WO 91/03162; Sproat, U.S. Pat. No. 5,334,711; Gold et al., U.S. Patent No. 6,300,074. All of the above references describe various chemical modifications that can be made to the base, phosphate, or sugar moieties of the tc-DNA AON described herein.

Formulation of Tricyclo-DNA for In vivo Administration

Tc-DNA AON described herein may be in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives.

Tc-DNA AON compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes tc-DNA AON compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences* (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

The present disclosure provides tc-DNA AON compositions and methods for facilitating exon skipping or masking intronic silencing or terminal stem loops in a pre-mRNA or for targeting the destruction of mRNA in a cell or organism. In related embodiments, this disclosure provides methods and tc-DNA AON compositions for treating a subject, including a human cell, tissue or individual, having a disease or at risk of developing a disease as described herein above. In one embodiment, the method includes administering a tc-DNA AON of this disclosure or a pharmaceutical composition containing the tc-DNA AON to a cell or an organism, such as a mammal, such that the processing of a pre-mRNA is modified or the destruction of an mRNA is targeted. Mammalian subjects amenable for treatment using the compositions and methods of the present disclosure include those suffering from one or more disorders which are amenable to such treatment such as, for example Duchenne Muscular Dystrophy, Spinal Muscular Atrophy, or Steinert's Myotonic Dystrophy.

The tc-DNA AON compositions of the instant disclosure can be effectively employed as pharmaceutically acceptable formulations. Pharmaceutically-acceptable formulations prevent, alter the occurrence or severity of, or treat (alleviate one or more symptom(s) to a detectable or measurable extent) of a disease state or other adverse condition in a patient. A pharmaceutically acceptable formulation includes salts of the above compounds, e.g., acid addition salts such as salts of hydrochloric acid, hydrobromic acid, acetic acid, and benzene sulfonic acid. A pharmaceutical composition or formulation refers to a composition or formulation in a form suitable for administration, e.g., systemic administration, into a cell or patient such as a human. Suitable forms, in part, depend upon the use or the route of entry, for example transdermal or by injection. Such forms should not prevent the composition or formulation from reaching a target cell (i.e. a cell to which the tc-DNA AON is desirable for delivery). For example, pharmaceutical compositions injected into the blood stream should be soluble. Other factors are known in the art, and include considerations such as toxicity and forms that prevent the composition or formulation from exerting its effect.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

The tc-DNA AON of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus tc-DNA AON of the present disclosure may be administered in any form, for example transdermally or by local, systemic, or intrathecal injection.

This disclosure also features the use of tc-DNA AON compositions comprising surface-modified liposomes containing poly(ethylene glycol) lipids (PEG-modified, or long-circulating liposomes or stealth liposomes). These formulations offer a method for increasing the accumulation of tc-DNA AON in target tissues. This class of drug carriers resists opsonization and elimination by the mononuclear phagocytic system (MPS or RES), thereby enabling longer blood circulation times and enhanced tissue exposure for the encapsulated tc-DNA AON (Lasic et al., *Chem. Rev.* 95:2601-2627 (1995) and Ishiwata et al., *Chem. Pharm. Bull.* 43:1005-1011 (1995). Long-circulating liposomes enhance the pharmacokinetics and pharmacodynamics of tc-DNA AON, particularly compared to conventional cationic liposomes which are known to accumulate in tissues of the MPS (Liu et al., *J. Biol. Chem.* 42:24864-24870 (1995); Choi et al., PCT Publication No. WO 96/10391; Ansell et al., PCT Publication No. WO 96/10390; Holland et al., PCT Publication No. WO 96/10392). Long-circulating liposomes are also likely to protect tc-DNA AON from nuclease degradation to a greater extent compared to cationic liposomes, based on their ability to avoid accumulation in metabolically aggressive MPS tissues such as the liver and spleen.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. For example, an amount between 0.1 mg/kg and 100 mg/kg body weight/day of active ingredients is administered dependent upon potency of the tc-DNA AON of this disclosure.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy. Following administration of tc-DNA AON compositions according to the formulations and methods of this disclosure, test subjects will exhibit about a 10% up to about a 99% reduction in one or more symptoms associated with the disease or disorder being treated, as compared to placebo-treated or other suitable control subjects.

Tc-DNA AON can be administered to cells by a variety of methods known to those of skill in the art, including administration within formulations that comprise the tc-DNA AON alone, or that further comprise one or more additional components, such as a pharmaceutically acceptable carrier, diluent, excipient, adjuvant, emulsifier, buffer, stabilizer, preservative, or the like. In certain embodiments, the tc-DNA AON can be encapsulated in liposomes, administered by iontophoresis, or incorporated into other vehicles, such as hydrogels, cyclodextrins, biodegradable nanocapsules, bioadhesive microspheres, or proteinaceous vectors (see, e.g., PCT Publication No. WO 00/53722).

Direct injection of the tc-DNA AON of this disclosure, whether subcutaneous, intramuscular, or intradermal, can take place using standard needle and syringe methodologies, or by needle-free technologies, such as those described in Conry et al., *Clin. Cancer Res.* 5:2330-2337 (1999), and PCT Publication No. WO 99/31262.

Further methods for delivery of nucleic acid molecules, such as the tc-DNA AON of this disclosure, are described, for example, in Boado et al., *J. Pharm. Sci.* 87:1308-1315 (1998); Tyler et al., *FEBS Lett.* 421:280-284 (1999); Pardridge et al., *Proc. Nat'l Acad. Sci. USA* 92:5592-5596 (1995); Boado, *Adv. Drug Delivery Rev.* 15:73-107 (1995); Aldrian-Herrada et al., *Nucleic Acids Res.* 26:4910-4916 (1998); Tyler et al., *Proc. Nat'l Acad. Sci. USA* 96:7053-7058 (1999); Akhtar et al., *Trends Cell Bio.* 2:139 (1992); "Delivery Strategies for Antisense Oligonucleotide Therapeutics," (ed. Akhtar, 1995); Maurer et al., *Mol. Membr. Biol.* 16:129-140 (1999); Hofland and Huang, *Handb. Exp. Pharmacol* 137:165-192 (1999); and Lee et al., *ACS Symp. Ser.* 752:184-192 (2000). These protocols can be utilized to supplement or complement delivery of virtually any tc-DNA AON contemplated within this disclosure.

EXAMPLES

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

Example 1

Use of Tricyclo-DNA Antisense Oligonucleotides to Rescue Dystrophin in Dystrophic Muscle Fibers Duchenne Muscular Dystrophy (DMD) is an X-linked recessive disorder that results from mutations in the gene encoding dystrophin. Out-of-frame deletions within the dystrophin gene that encode a truncated dystrophin protein deficiency lead to severe DMD phenotypes. Exon-skipping strategies using tricyclo-DNA (tc-DNA) antisense oligonucleotides (AON) were developed to permit the efficient rescue of out-of-frame dystrophin gene mutations thereby restoring the translational reading-frame and hence the production of functionally active dystrophin protein. Tc-DNA AON are described that, for example, hybridize to an exon 23/intron 23 junction and interfere with pre-mRNA processing such that exon 23 is spliced out of the resulting processed mRNA. Alternatively, tc-DNA AON that hybridize to an exon 51/intron 51 junction similarly interfere with pre-mRNA processing such that exon 51 is spliced out of the processed mRNA. The resulting dystrophin proteins are thus deleted in amino acid sequences encoded by exon 23 or exon 51, respectively, yet retain sufficient functionality such that the severe DMD phenotype is reversed.

Example 2

The mdx Mouse Model

Figure 3:
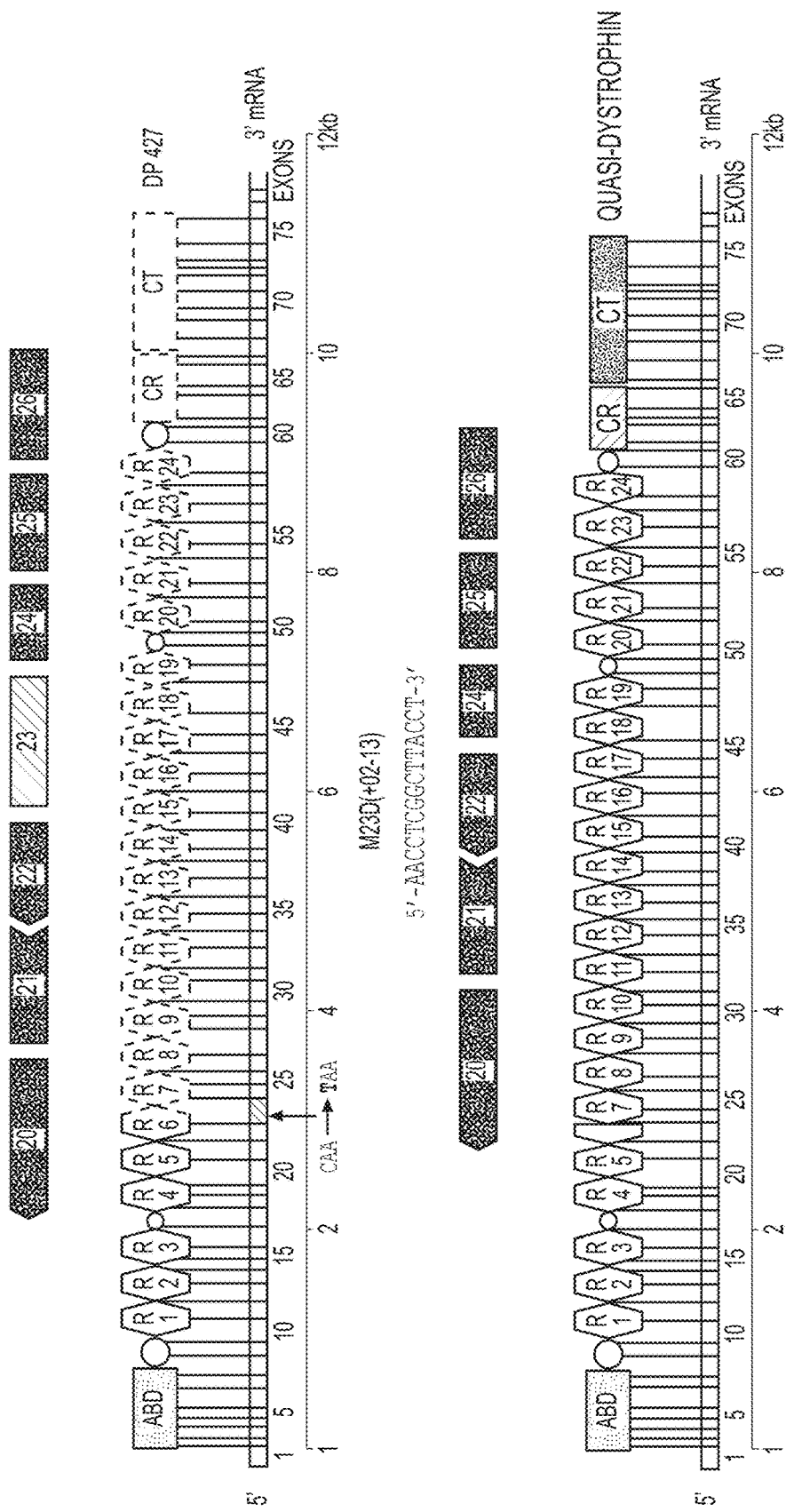
FIG. 3 is a diagram showing that the mdx mouse carries a non-sense mutation in exon 23 of the dystrophin gene, which precludes synthesis of functional dystrophin. Exon 23 partially encodes repeats R6 and R7 in which a C to T mutation creates a stop codon (TAA). The 15 nucleotide tc-DNA AON for exon skipping at the downstream donor splice site of exon 23, designated M23D (+02-13) has the nucleotide sequence 5'-AACCTCGGCTTACCT-3' (SEQ ID NO: 1) and hybridizes to the target dystrophin pre-mRNA exon 23/intron 23 junction, which is defined by the sequence 5'-exon 23 . . . TCAGgtaagccgaggifiggcc . . . intron 23-3' (SEQ ID NO: 2), where capital letters designate exonic nucleotides and lower-case letters designate intronic nucleotides.

The mdx mouse is a murine model of DMD that lacks the full length dystrophin protein, but retains all the smaller dystrophin isoforms. Bulfield et al., *Proc. Natl. Acad. Sci. USA* 81:1189-1192 (1984). The mdx mouse carries a nonsense mutation in exon 23 of the dystrophin gene, which precludes functional dystrophin synthesis (see, FIG. 3). Exon 23 partially encodes repeats R6 and R7 in which a C to T mutation creates a stop codon (TAA).

Example 3

In vitro Studies

This example demonstrates that mdx myotubes transfected with a 15-nucleotide tc-DNA AON designated M23D (+02-13) having the nucleotide sequence 5'-AACCTCG-GCTTACCT-3' undergo exon skipping at the downstream donor splice site of exon 23 such that dystrophin pre-mRNA is processed to mRNA that are deleted in exon 23.

The tc-DNA AON designated M23D (+02-13), was designed such that it hybridizes to the target sequence intron 22-ttttgag[GCTC . . . EXON 23 . . . TCAG]gtaagccgaggtttg-gcc-intron 23 at the exon 23/intron 23 splice junction.

Mdx myotubes were transfected with tc-DNA AON M23D (+02-13) (1, 2 and 10 µg) with or without oligofectamine. One sample was left untreated, as a negative control. After 48 hours, cultures were harvested and mRNA was extracted using the RNeasy mini kit (Qiagen). mRNA was then reverse transcribed, as follows. Eight microliters of extracted RNA (500 ng to 1 µg) was mixed with 1 µL dNTP and 1 µL random hexamers, and the mixture was incubated for 5 minutes at 65° C. The mixture was then cooled on ice. 25 mM MgCl$_2$ (4 µL), 0.1 M DTT (2 µL), 1 µL RNase out ribonuclease inhibitor (40 U/µL), 1X Tampon (2 µL of 10× stock) and 50U SuperScript reverse transcriptase were added to the mixture to bring the reaction to a final volume of 20 µL. The reaction was then incubated for 10 minutes at 25° C., followed by 50 minutes at 42° C. Next, the reaction was inactivated by heating for 15 minutes at 70° C. The reaction was then placed on ice and vortexed. One µL of RNase H was then added to the reaction, and incubated at 37° C. for 20 minutes.

Next, the skipping of exon 23 was assayed by nested PCR, using the following conditions. Twenty five µL it PCR master mix (Taq polymerase 50U/µL, 400 µM dNTPs, 3 mM MgCl$_2$) was combined with 3 µL cDNA, 22 µL H$_2$0 and 1 µL each of the following two primers (100 µM stock concentration):

```
Ex 20 Fo
5'-CAGAATTCTGCCAATTGCTGAG-3'

Ex 26 Ro
5'-TTCTTCAGCTTGTGTCATCC-3'
```

The reaction was then subjected to the following thermal cycling parameters. Five min. at 94° C., followed by thirty cycles of 30 sec. 94° C., 1 min. 55° C. and 2 min. at 72° C. Finally, the reaction is subjected to a five minute incubation at 72° C.

Two microliters of the PCR product was added to another PCR reaction as template, using 1 µL, of the following primers (100 µM stock concentration). The reaction also included 25 µL PCR master mix and 23 µL H$_2$O.

```
Ex 20 Fi
5'-CCCAGTCTACCACCCTATCAGAGC-3'

Ex 26 Ri
5'-CCTGCCTTTAAGGCTTCCTT-3'
```

The reaction was subjected to the following thermal cycling parameters—Five min. at 94° C., followed by twenty five cycles of 30 sec. 94° C., 1 min. 55° C. and 2 min. at 72° C. Finally, the reaction was subjected to a five minute incubation at 72° C.

Figure 4:
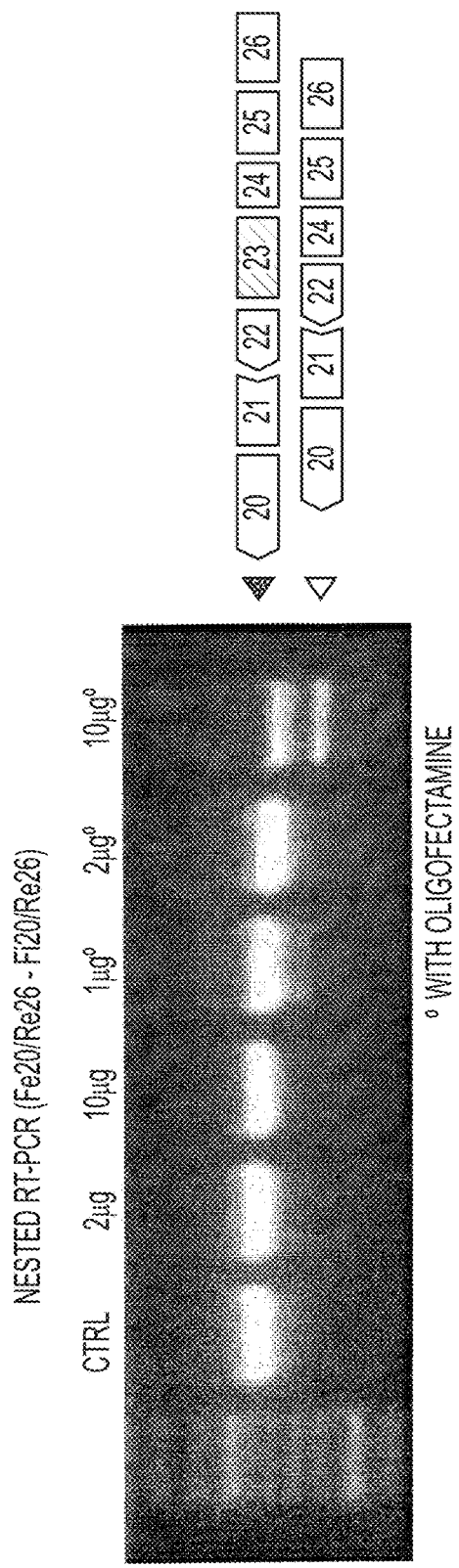
FIG. 4 is an agarose gel of nested RT-PCR reactions showing the skipping of dystrophin pre-mRNA exon 23 in mdx myotubes transfected, with or without oligofectaminc, with 1, 2, and 10 µg of tc-DNA AON M23D (+02-13). After 48 hours, cultures were harvested and processed for mRNA extraction.

The data presented in FIG. 4 demonstrate that: (1) the 15 nucleotide tc-DNA AON M23D (+02-13) can achieve skipping of the mutated exon 23 in the dystrophin mRNA of mdx ex vivo and (2) oligofectamine improves tc-DNA AON uptake ex vivo.

Figure 5:
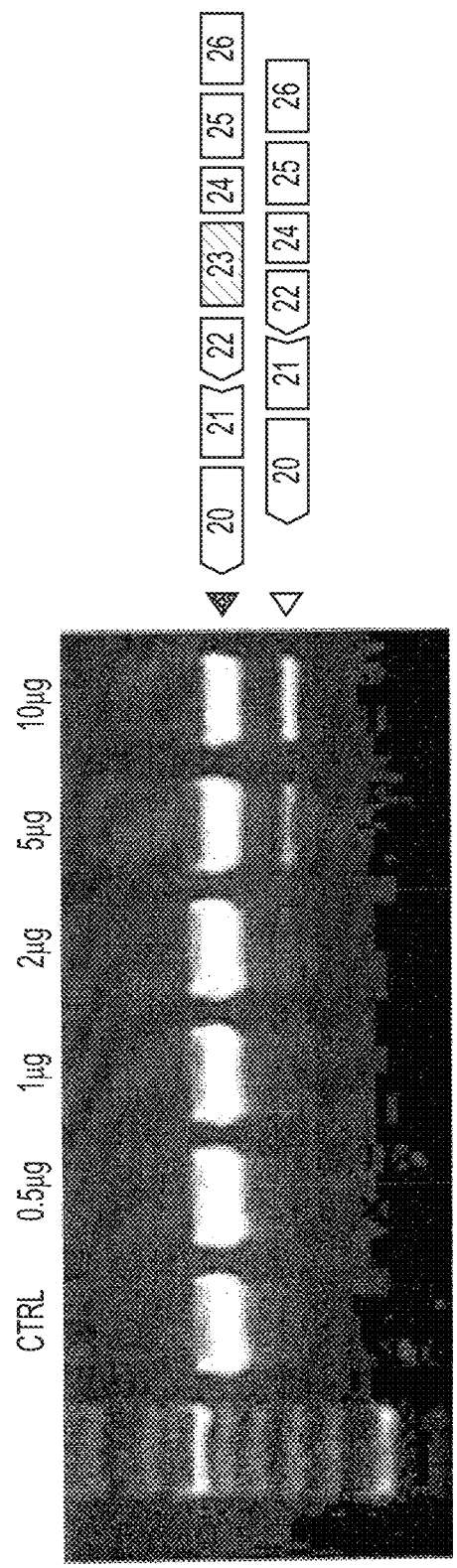
FIG. 5 is an agarose gel of nested RT-PCR reactions showing the skipping of dystrophin pre-mRNA exon 23 in mdx myotubes transfected with 0.5, 1, 2, 5 and 10pg of tc-DNA AON M23D (+02-13) in the presence of oligofectamine. After 48 hours, cultures were harvested and processed for mRNA extraction.

Mdx myotubes were transfected with tc-DNA AON M23D (+02-13) (0.5, 1, 2, 5 and 10 µg) in the presence of oligofectamine. Cultures were processed as described above. The data presented in FIG. 5 demonstrate that skipping is noticeable in the presence of 2 µg of tc-DNA AON M23D (+02-13).

Figure 6:
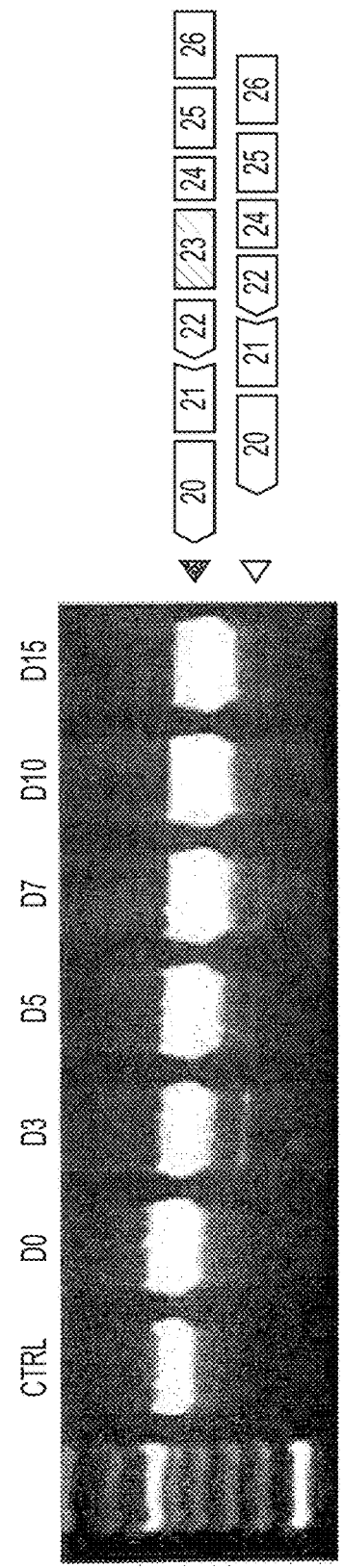
FIG. 6 is an agarose gel of nested RT-PCR reactions showing the skipping of dystrophin pre-mRNA exon 23 in mdx myotubes transfected with 5µg of tc-DNA AON M23D (+02-13) in the presence of oligofectamine. Cultures were harvested and processed for mRNA extraction from day 0 to day 15 after transfection.

Mdx myotubes were transfected with 5 µg of tc-DNA AON M23D (+02-13) in the presence of oligofectamine. Cultures were processed as described above at different time points after transfection (from day 0 to day 15). The data presented in FIG. 6 demonstrate that: (1) skipping was observed at day 3 (D3) and (2) skipping was still detectable at day 15 (D15) but decreased from day 7 (D7).

Example 4

In vivo Studies

This example demonstrates that mdx mice injected with a 15-nucleotide tc-DNA AON designated M23D (+02-13) having the nucleotide sequence 5'-AACCTCGGCTTACCT-3' undergo exon skipping at the downstream donor splice site of exon 23 such that dystrophin pre-mRNA is processed to mRNA that are deleted in exon 23.

Eight-week-old mdx mice were injected in the tibialis anterior muscle with 50 µl PBS (phosphate buffer saline) containing 100, 80, 40, 20, 10 and 5 µg of tc-DNA AON M23D (+02-13). Animals were sacrificed 3 weeks later. Muscle samples were processed for mRNA analysis using the same parameters given above for example 3, and the results are given in FIG. 7.

Figure 7:
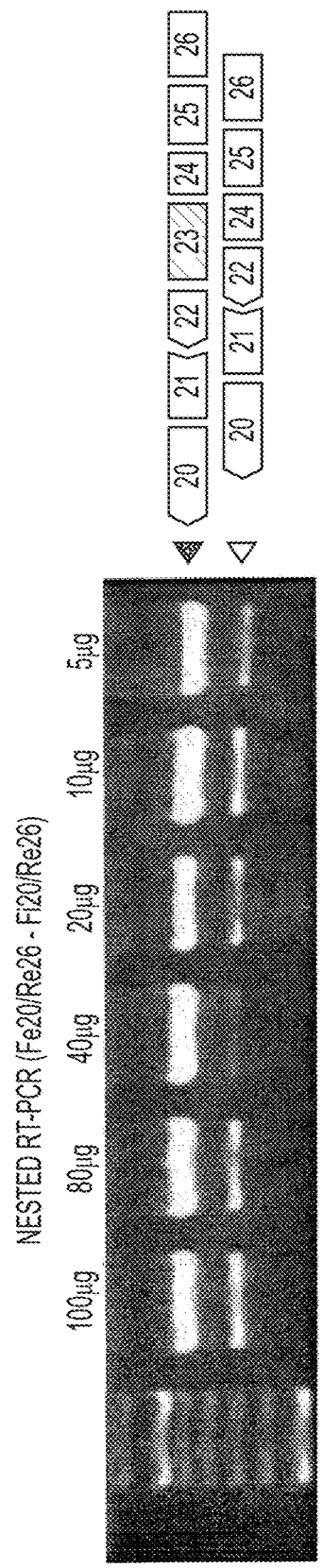
FIG. 7 is an agarose gel of nested RT-PCR reactions showing the skipping of dystrophin pre-mRNA exon 23 in eight week old mdx mice injected in the tibialis anterior muscle with 50 µl PBS (phosphate buffer saline) containing 100, 80, 40, 20, 10 and 5 µg of tc-DNA AON M23D (+02-13). Animals were sacrificed 3 weeks later and muscle samples processed for mRNA analysis.

The data presented in FIG. 7 demonstrate that exon skipping occurred in all conditions tested. Also, significant levels of dystrophin protein were detected in transverse sections (not shown). Injection of 2 µg tc-DNA AON M23D (+02-13) was equivalent to 5 µg tc-DNA AON M23D (+02-13) (not shown).

Eight week old mdx mice were injected intramuscularly with 50 µl PBS containing 10 µg tc-DNA AON M23D (+02-13). Animals were sacrificed at 4, 10, and 20 weeks after injection. Muscle samples and transverse sections were assayed for dystrophin mRNA, as described above. The results are presented in FIG. 8.

Muscle transverse sections were assayed for dystrophin protein expression using immunostaining, as follows. Primary monoclonal antibody NCL-Dys 2 (1:100 dilution) was added to the samples, using the M.O.M. (mouse on mouse) kit. The samples were then washed 3 times in PBS. The samples were then incubated with secondary antibody goat anti-mouse IgG, labeled with Alexa Fluor 488 (Molecular Probes) for two hours, followed by a PBS wash, a 0.01% TritanX wash and a final PBS wash. The results of this experiment are given in FIG. 9.

Figure 8:
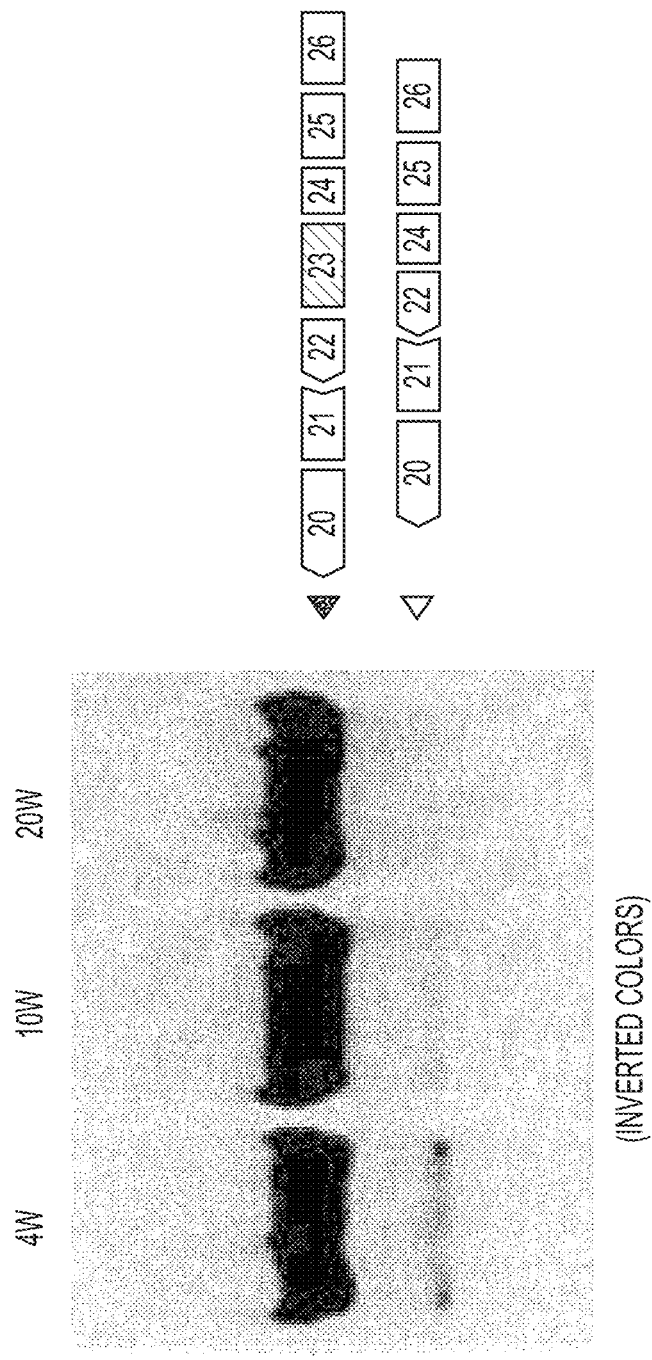
FIG. 8 is an agarose gel of RT-PCR reactions showing the skipping of dystrophin pre-mRNA exon 23 in eight week old mdx mice injected in the tibialis anterior muscle with 50 µl PBS (phosphate buffer saline) containing 10 µg of tc-DNA AON M23D (+02-13). Animals were sacrificed 4, 10, and 20 weeks later and muscle samples processed for mRNA analysis.
Figure 9:
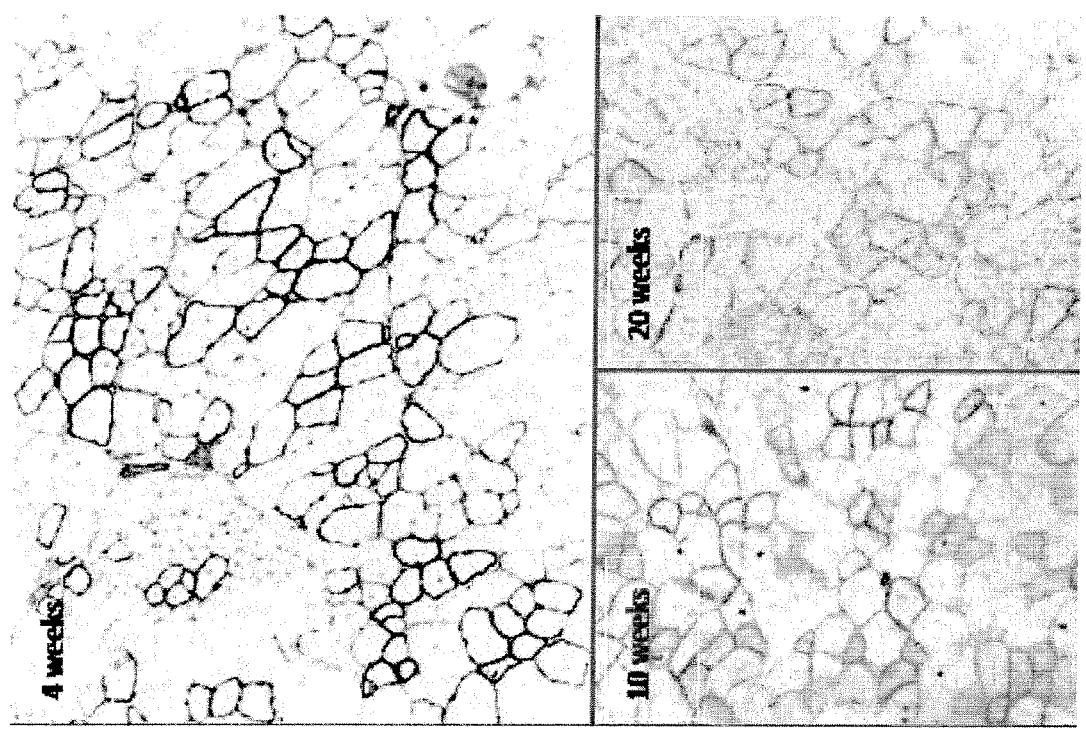
FIG. 9 is a photomicrograph of immune-staining of dystrophin in transverse sections of tibialis anterior muscle tissue from mdx mice injected at eight weeks with 50 µl PBS (phosphate buffer saline) containing 10 µg of tc-DNA AON M23D (+02-13). Animals were sacrificed 4, 10, and 20 weeks later and muscle samples processed for immuno-staining

The data presented in FIGS. 8 and 9 demonstrate that (1) exon skipping was apparent at 4 and 10 weeks but was not observed at 20 weeks; (2) dystrophin is clearly detectable from 4 weeks through 20 weeks; and (3) tc-DNA AON M23D (+02-13) appears more efficient in vivo than ex vivo.

Example 5

Brain Immunostaining

Figure 10:
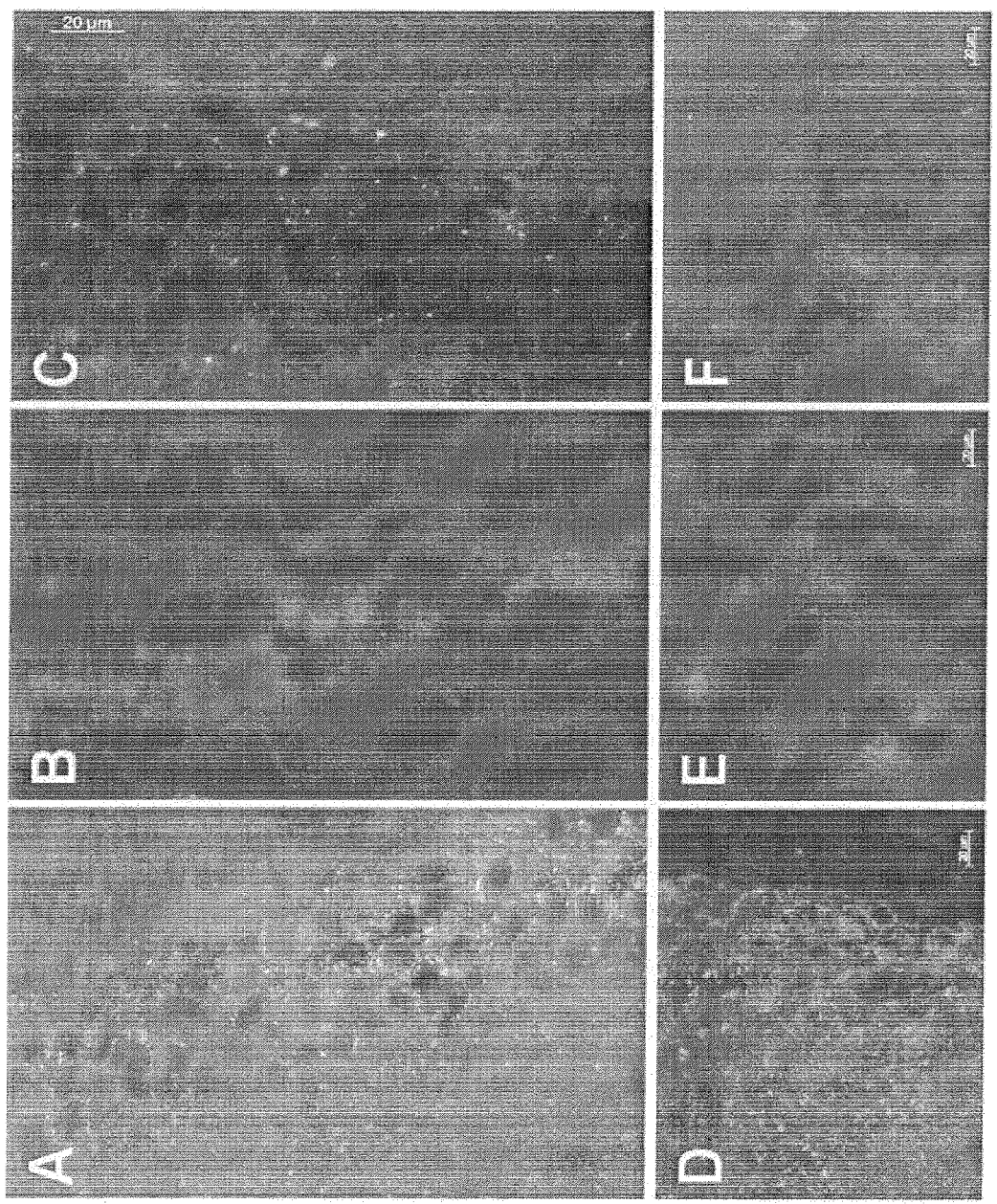
FIGS. 10A-F are an immune-staining of dystrophin in the CNS of normal and mdx mouse injected with tc-DNA AON M23D (+02-13) into the hippocampus or into the cerebrospinal fluid.

Eight week old mdx mice were injected in the hippocampus or the cerebro-spinal fluid (intrathecal injection) with 50 µl PBS containing 20 µg (hippocampus) or 200µg (intrathecal) tc-DNA AON M23D (+02-13). Animals were sacrificed one month after injection. Brain sections (panels A,B,C) and cerebellar sections (panels D,E,F) were assayed for dystrophin protein, as described above in Example 4. The results are presented in FIG. 10. Panels A and D correspond to negative controls, where the mice were not treated. Panels B and E correspond to untreated section from an mdx mouse. Panel C corresponds to a hippocampus-treated mdx mouse (C), and panel (F) shows the results from an intrathecal-treated cerebellum of mdx mouse. Nuclei were counterstained with DAPI.

Example 6

Delivery (Prophetic)

Tc-DNA AON M23D (+01-13) may be delivered through intraperitoneal and subcutaneous injections (from 1g/kg and below).

Example 7

Tricyclo-DNA Antisense Oligonucleotides for Dystrophin Rescue in DMD Mice

This example demonstrates that tc-DNA AON designed for the dystrophin exon 51/intron 51 junction having the sequences 5'-AGAAATGCCATCTTC-3' ("tc-DNA AON H51 (+68+82)", SEQ ID NO: 2), 5'-AAATGCCATCT-TCCT-3' ("tc-DNA AON H51 (+70+84)"; SEQ ID NO: 3), and 5'-TGCCATCTTCCTTGA-3' ("tc-DNA AON H51 (+73+87)"; SEQ ID NO: 4), effectively mediated the skipping of exon 51 in muscle cells from mice expressing the full human dystrophin gene ("hDMD mice").

Eight to ten-week-old hDMD mice were injected in the tibialis anterior muscle with 50 µl PBS containing 10 µg of tc-DNA AON H51 (+68+82) also referred to as Tc-DNA ex51 ESEa, tc-DNA AON H51 (+70+84) also referred to as Tc-DNA ex51 ESEb, or tc-DNA AON H51 (+73+87) also referred to as Tc-DNA ex51 ESEc. Animals were sacrificed 4 weeks later. Muscle samples were processed for mRNA analysis using the same parameters given above for example 3, and the results are given in FIG. 12.

The skipping of exon 51 was assayed by nested PCR under the following conditions. Five-hundred nanograms of total RNA were used for RT-PCR using the Access RT-PCR System (Promega) in a 50 µL reaction with the following external primers:

```
Hex 49F2
(5'-AAACTGAAATAGCAGTTCAAGC-3')

Hex 53R2
(5'-TTGCCTCCGGTTCTGAAGG-3')
```

The cDNA synthesis was carried out at 45° C. for 45 min, directly followed by primary PCR for 20 cycles with the following parameters: twenty cycles of 40 sec. at 94° C., 40 sec. at 60° C., and 40 sec at 72° C.

Two microliters of the PCR product were added to another PCR reaction as template, using the following primers (100 µM stock concentration).

```
Hex 50F
5'-AGGAAGTTAGAAGATCTGAGC-3'

Hex 52R2
5'-TTCTTCCAACTGGGGACGC-3'
```

The reaction was subjected to the following thermal cycling parameters: Five min. at 94° C., followed by thirty cycles of 40 sec. at 94° C., 40 sec. at 60° C., and 40 sec at 72° C. Finally, the reaction was subjected to a five minute incubation at 72° C.

Figure 12:
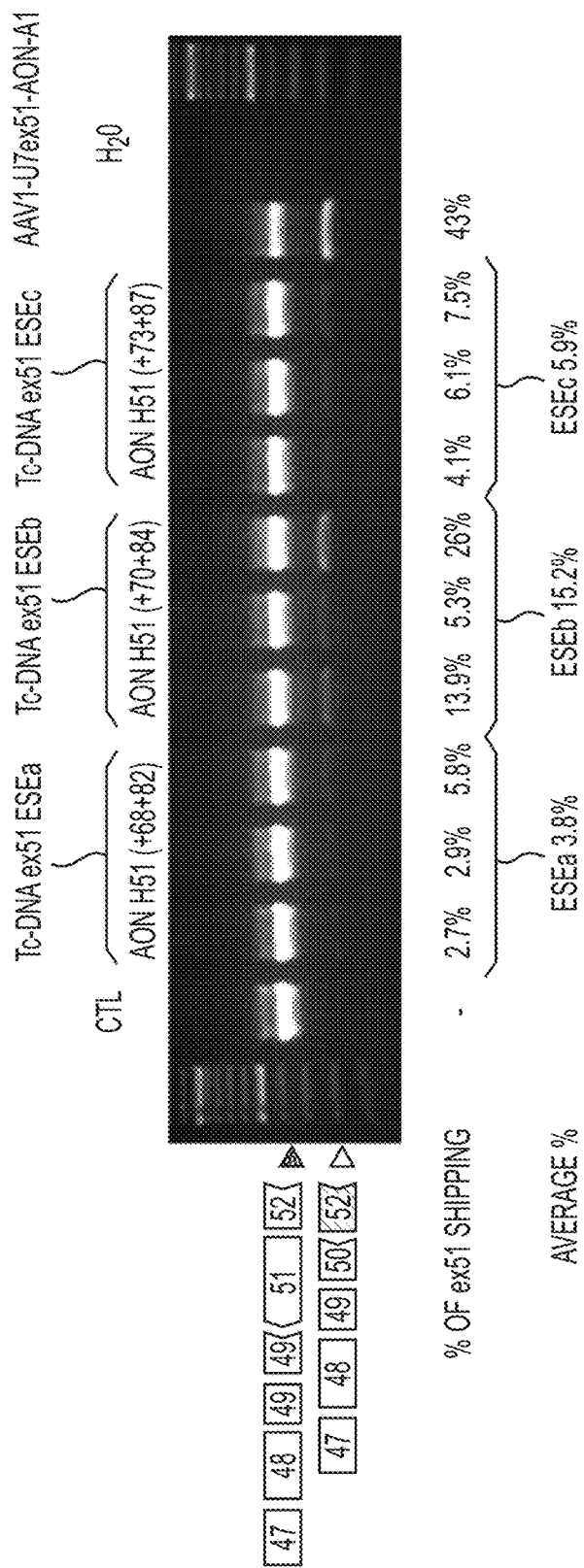
FIG. 12 is an agarose gel of nested RT-PCR reactions showing the skipping of dystrophin pre-mRNA exon 51 in eight to ten-week-old hDMD mice injected in the tibialis anterior muscle with 50 µl PBS (phosphate buffer saline) containing various tc-DNA AON.
Figure 13:
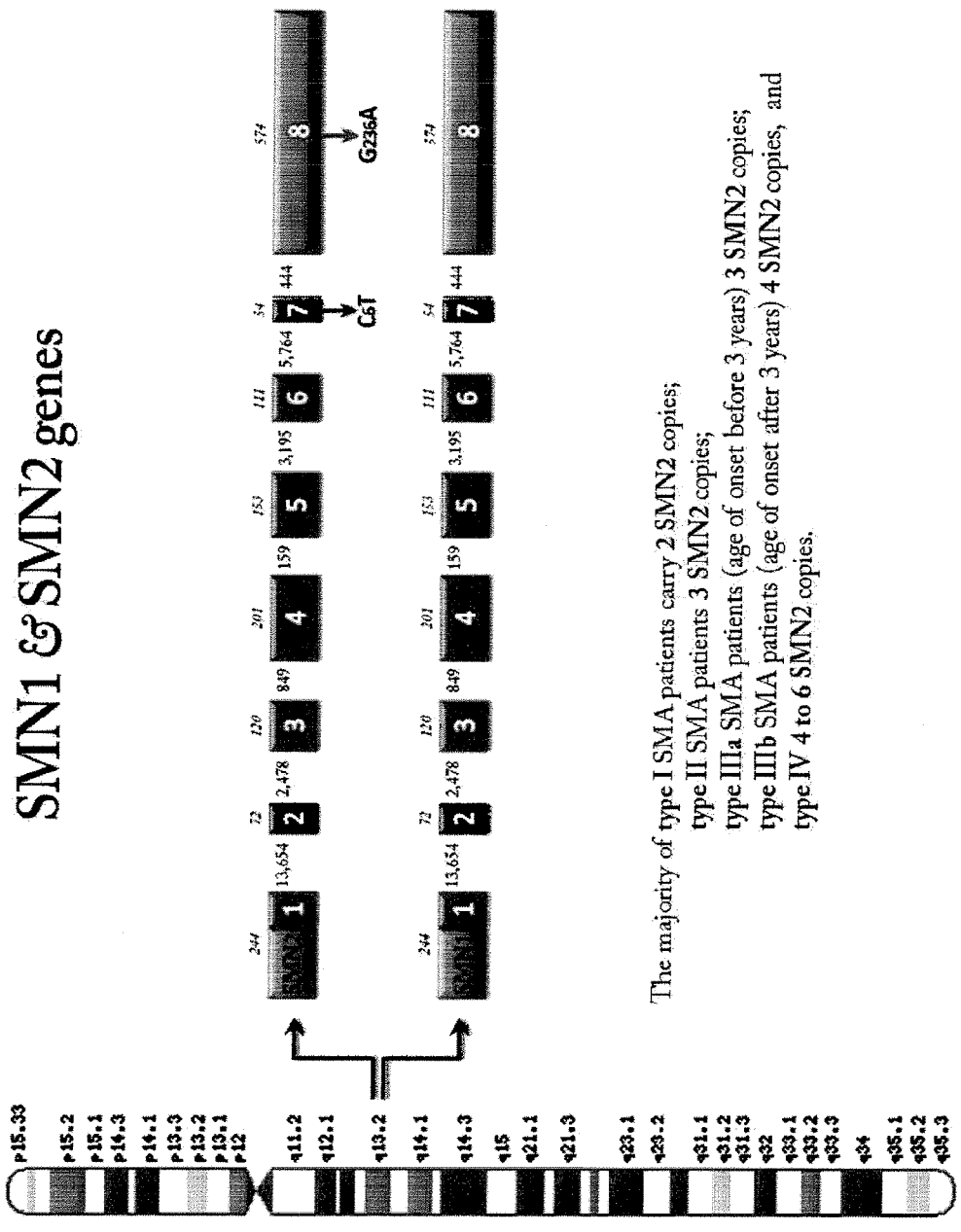
FIG. 13 is a diagrammatic representation of the intron-exon structures and chromosomal location of SMN1 and SMN2 genes.
Figure 14:
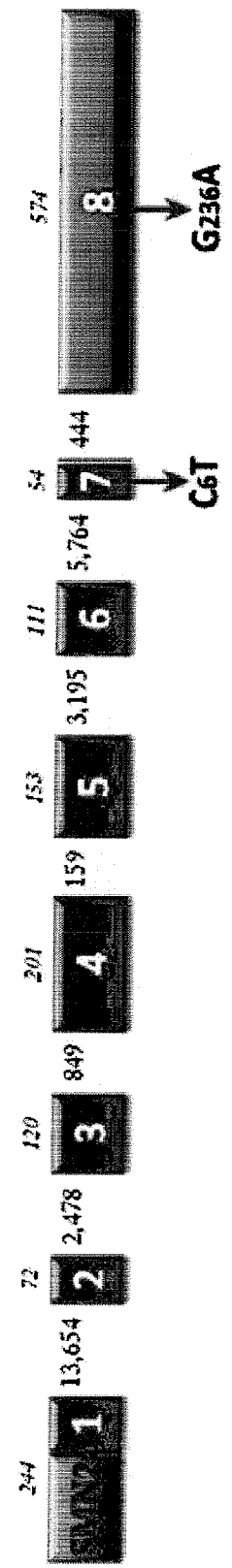
FIG. 14 is a diagrammatic representation of the point mutation (C6T) in SMN2, which predominantly lacks exon 7, that affects mRNA splicing.
Figure 15:
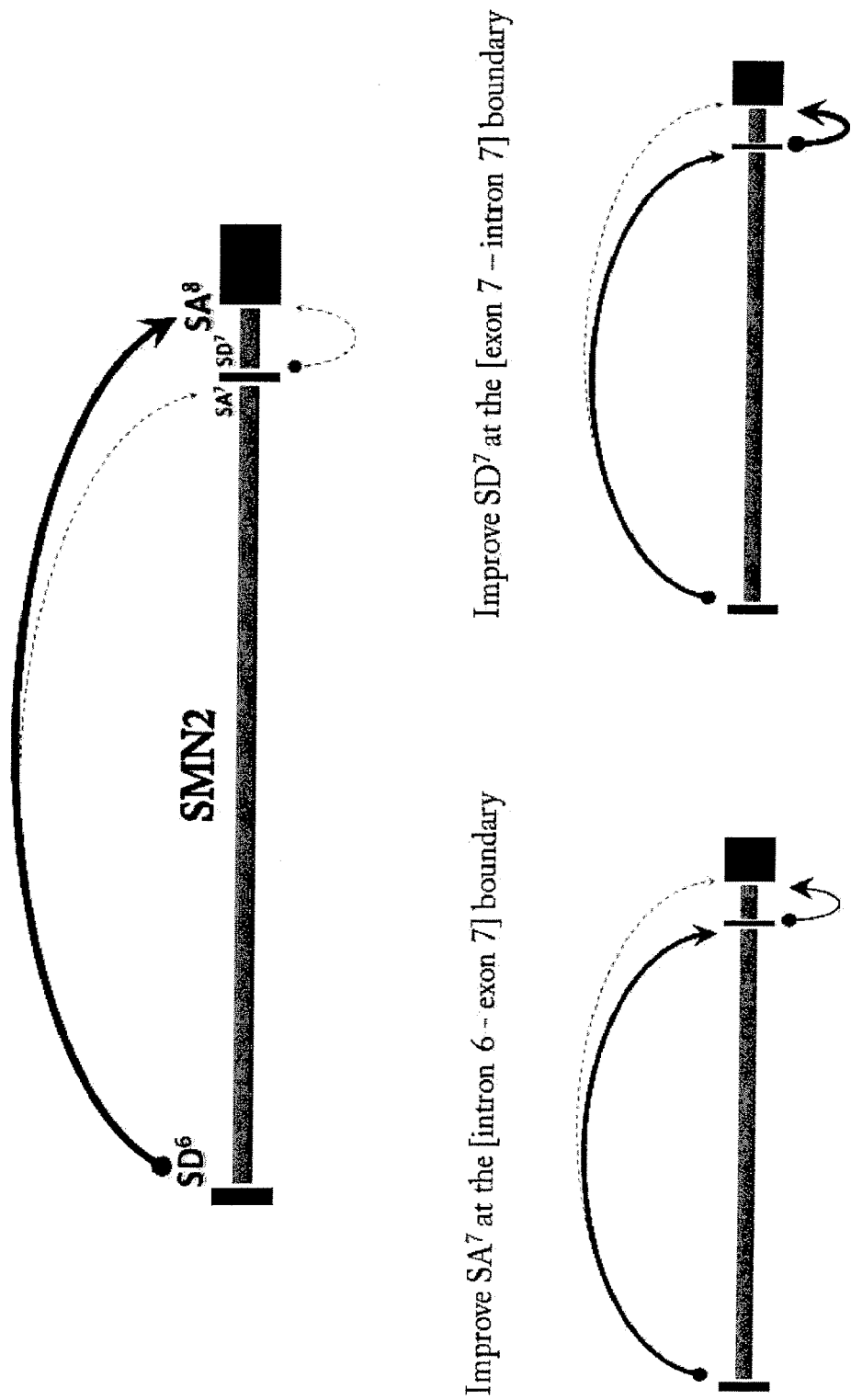
FIG. 15 is a diagrammatic representation of enhanced exon 7 inclusion in SMN2 by improving the use of splice acceptor ("SA") 7 at the intron 6-exon 7 boundary, and splice donor (SD) 7 at the exon 7-intron 7 boundary.
Figure 16:
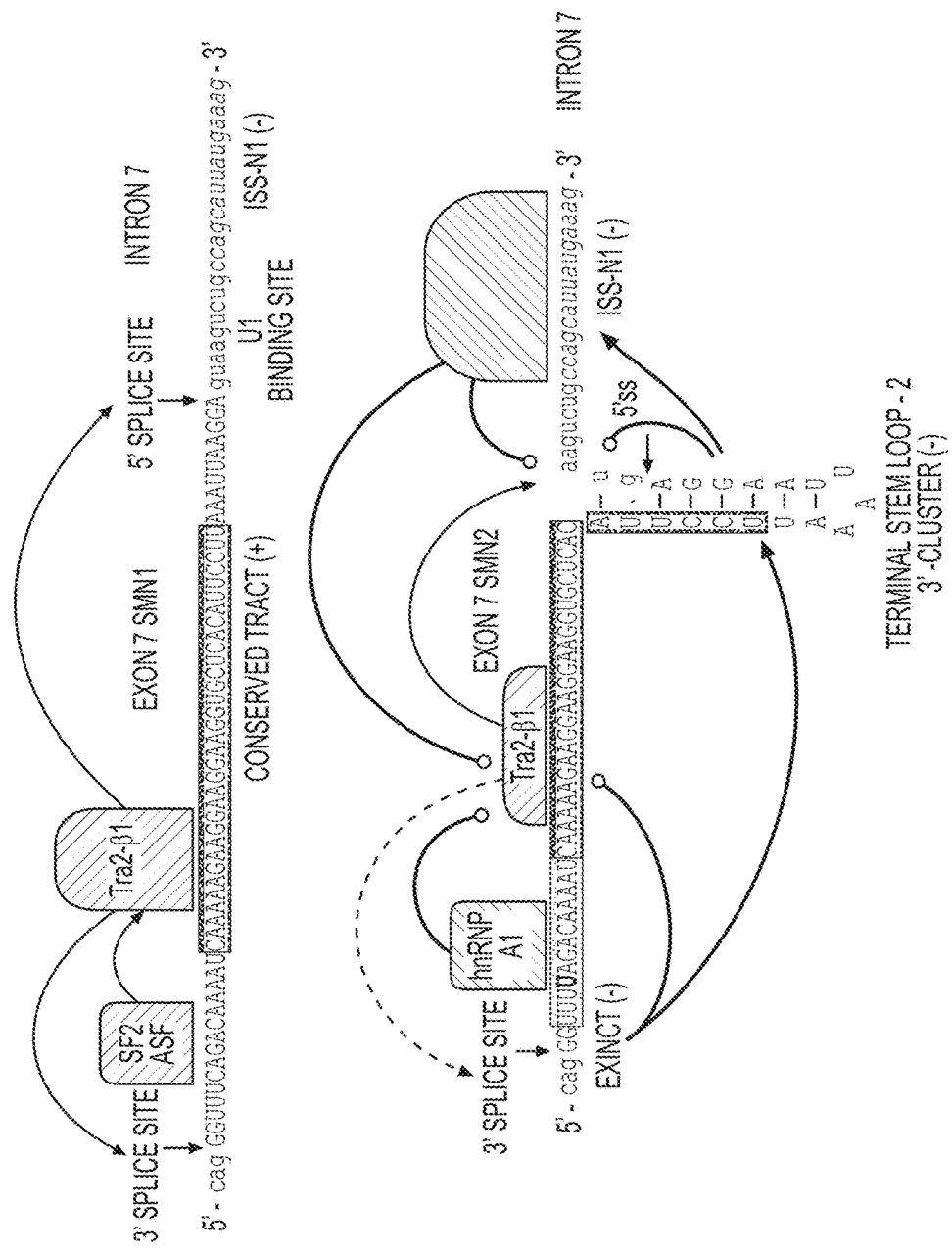
FIG. 16 is a diagrammatic representation of the structure of exon 7 in SMN1 and SMN2.
Figure 17:
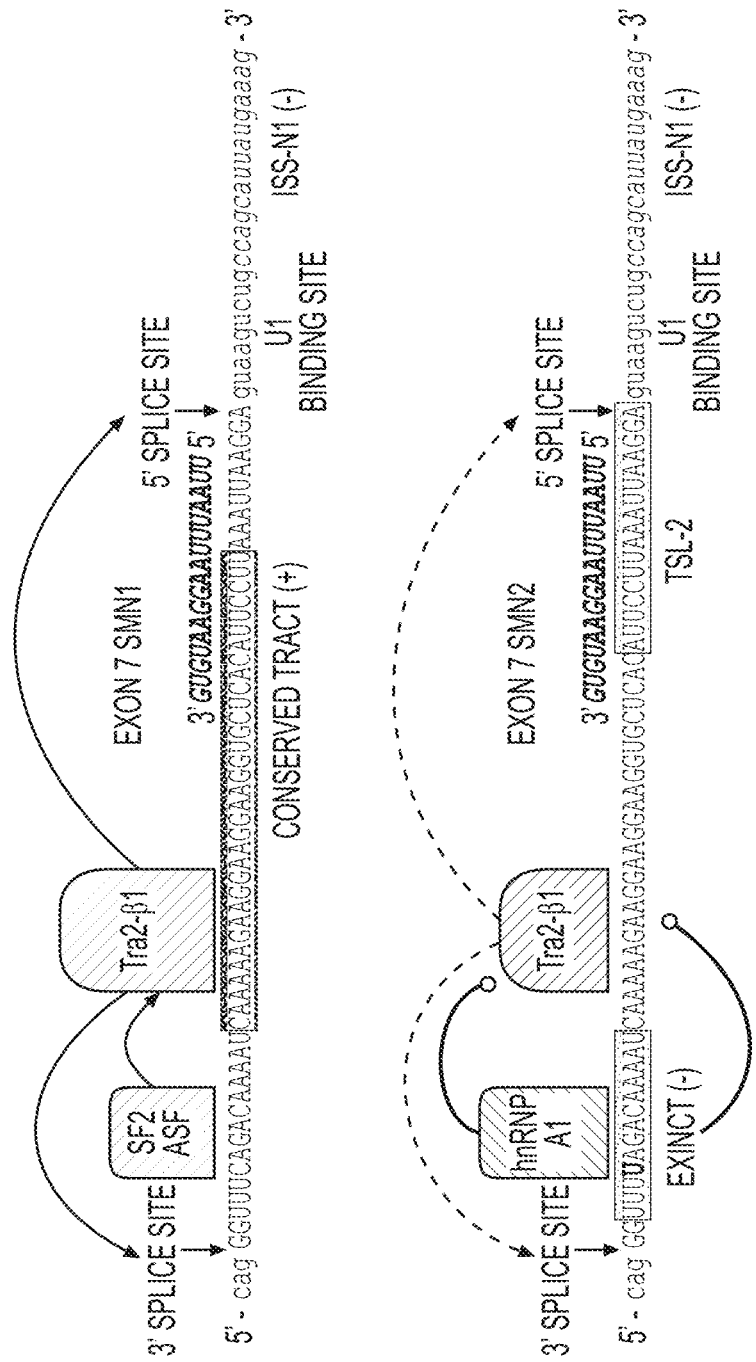
FIG. 17 is a diagrammatic representation of a target sequence and putative effects of tc-DNA AON SMN2e7 (39;51) (SEQ ID NO: 6) on SMN1 and SMN2 exon 7 structure. Tc- DNA AON SMN2e7(39;51), with the sequence 5'-UUAAUUUAAGGAAUGUG-3' (SEQ ID NO: 11), likely disrupts the structure of terminal stem loop 2 in SMN2, thereby enhancing exon 7 inclusion in SMN1 and SMN2.
Figure 18:
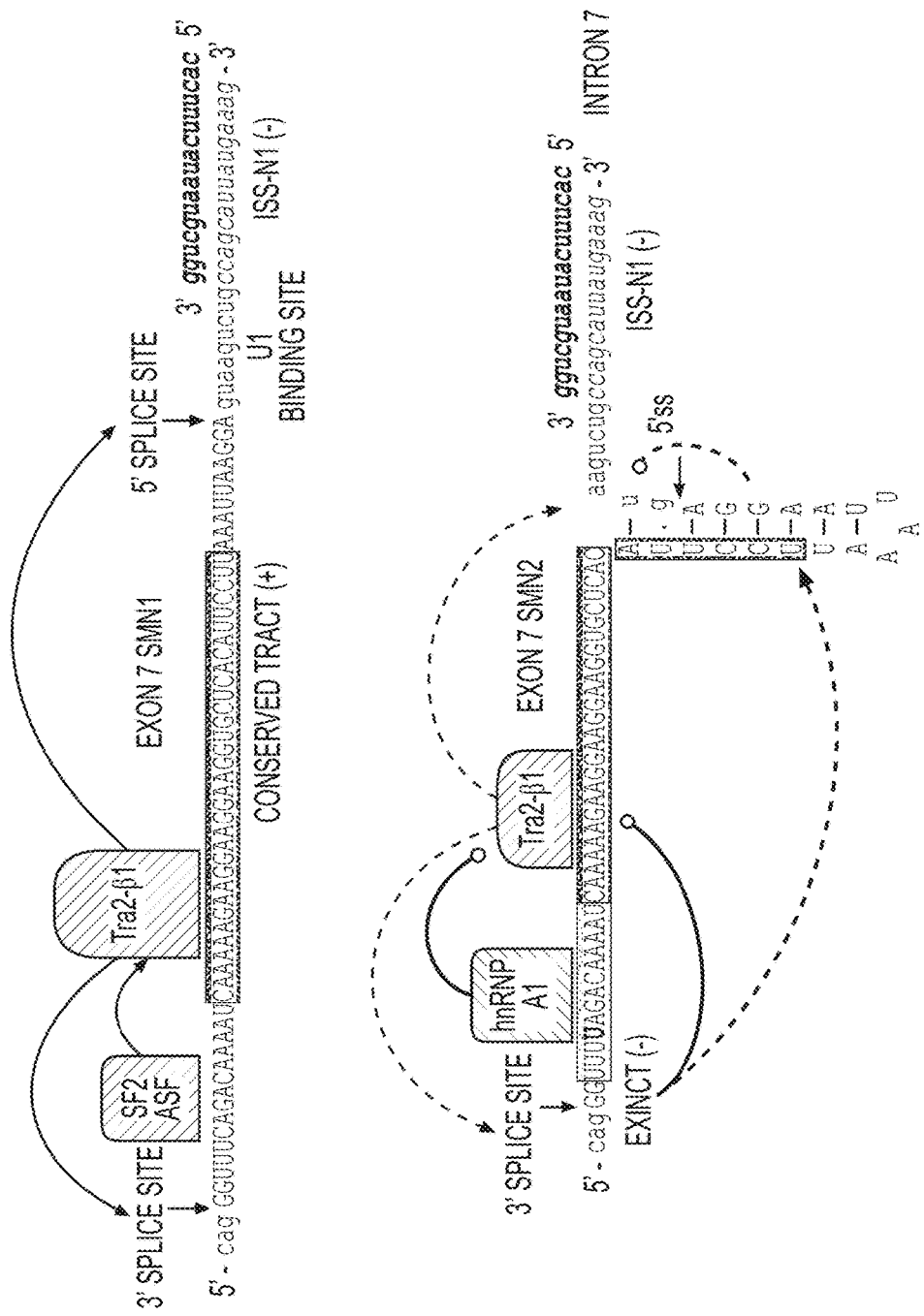
FIG. 18 is a diagrammatic representation of a target sequence and putative effects of tc-DNA AON SMN2i7(10; 25) (SEQ ID NO: 5) on SMN1 and SMN2 exon 7 inclusion. Tc-DNA AON SMN2i7 (10;25), with the sequence 5'-CACUUUCAUAAUGCUGG-3' (SEQ ID NO: 12), likely prevents recognition of the intronic silencer sequence ("ISS")-N1, allowing for recognition of the 5' splice site at the exon 7-intron 7 boundary. EXINCT refers to EXtended INhibitory ConteXT. Based on extensive mutation analysis, C6U has been shown to create an extended inhibitory context affecting exon 7 definition.
Figure 19A:
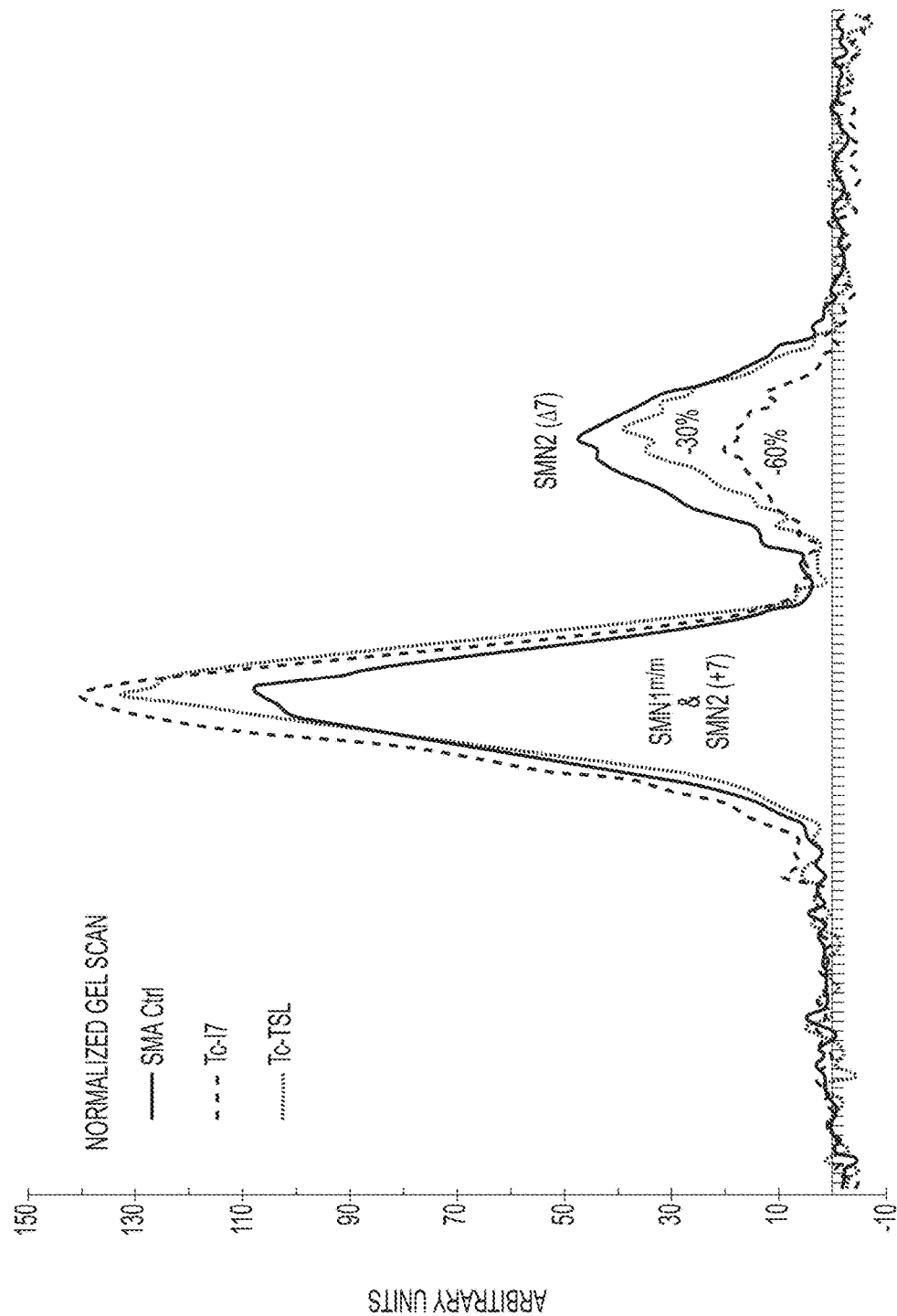
FIGS. 19A-B are an agarose gel of RT-PCR reactions (FIG. 19B) and a normalized plot (FIG. 19A) showing the inclusion of exon 7 in SMN2 in fibroblasts from an SMA patient (G03813 cell line). After 48 hours, cultures were harvested and processed for mRNA extraction. The plain line corresponds to mock treated control cells, the discontinued line corresponds to tc-DNA AON SMN2i7 (10;25) (referred to as tc-17) treated cells, and the dotted line corresponds to tc-DNA AON SMN2e7(39;51) (referred to as tc-TSL) treated cells. Plots have been normalized according to the total amount of SMN1+SMN2 (full length)+SMN2 (47) in each lane.
Figure 19B:
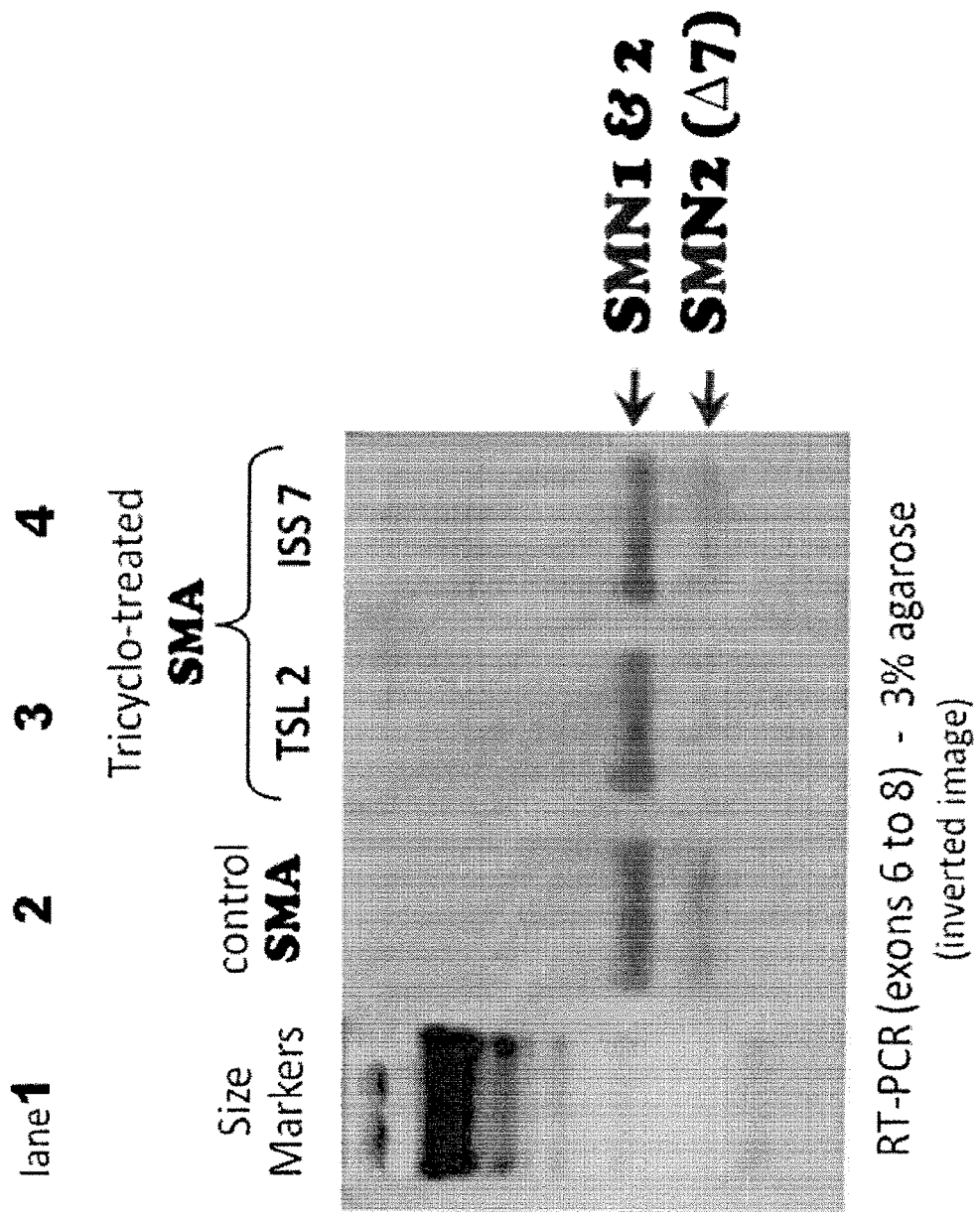
Figure 19C:
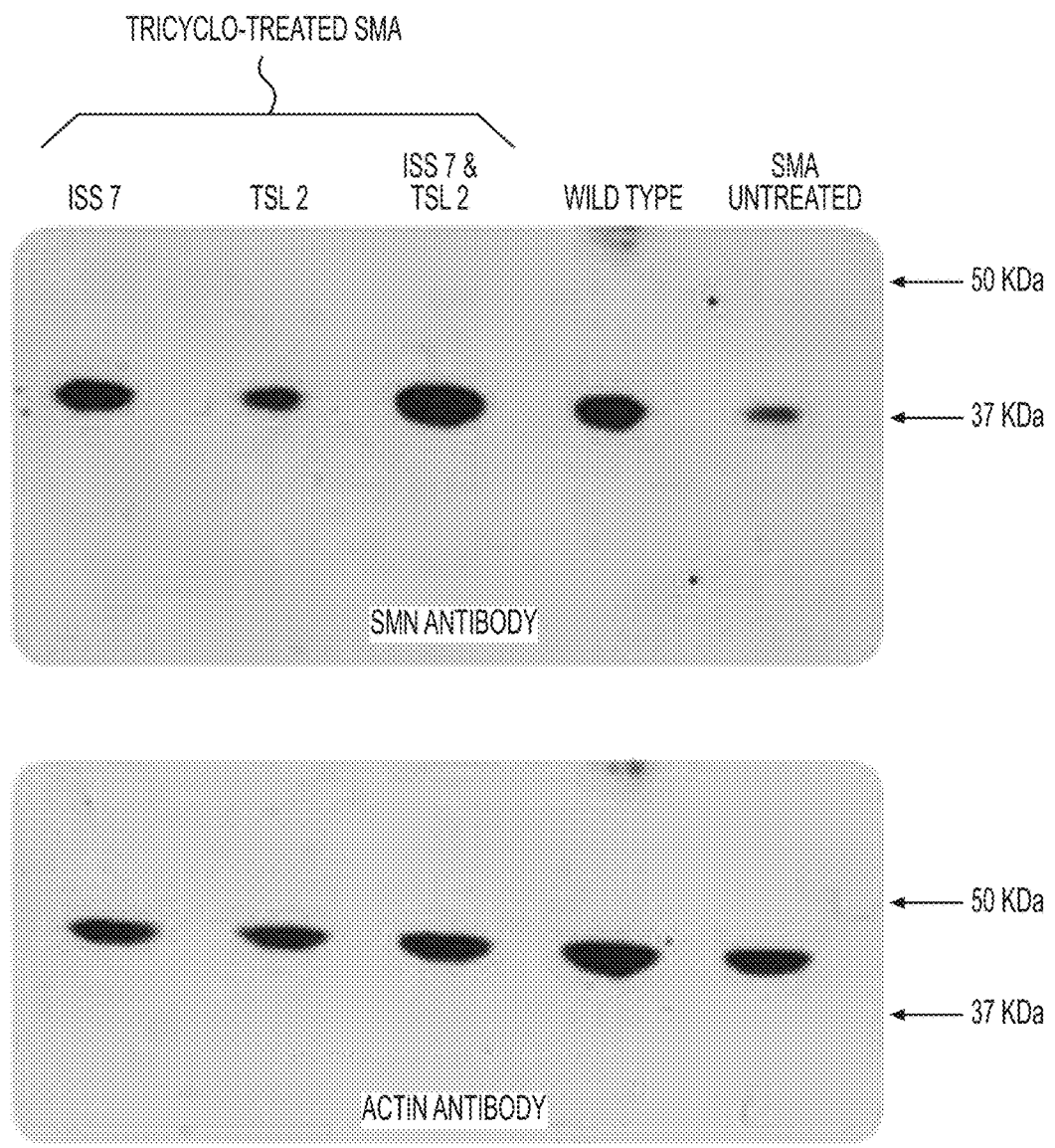
FIG. 19C is a Western blot showing levels of SMN in G03813 cells transfected with the indicated tc-DNA oligonucleotides. Actin is shown as a loading control. Of note is the additive effect of tc-DNA AON SMN2i7 (10;25) (referred to as tc-ISS7) and tc-DNA AON SMN2e7 (39;51) (referred to as tc-TSL) on SMN2 production.
Figure 19D:
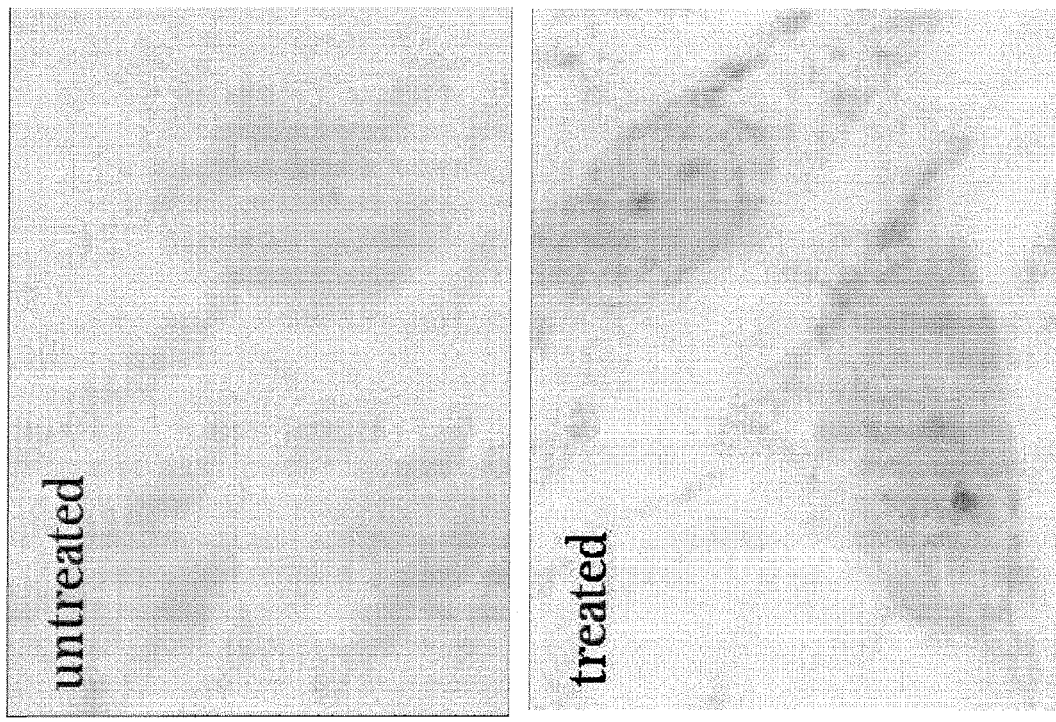
FIG. 19D is a photomicrograph showing the nuclear localization of SMN in tc-TSL treated cells (dark dots). Nuclei are counterstained with DAPI

The data presented in FIG. 12 demonstrate that each tc-DNA AON H51 construct tested (tc-DNA AON H51 (+68+82), tc-DNA AON H51 (+70+84), and tc-DNA AON H51 (+73+87)) resulted in increased exon 51 skipping.

Example 8

Tricyclo-DNA Antisense Oligonucleotides directed to the SMN exon 7/intron 7 junction and intron 7 ISS promote exon 7 inclusion in SMN2

This example demonstrates that tc-DNA AON designed for the SMN exon 7/intron 7 junction and intron 7 ISS ("tc-DNA AON SMN2e7(39;51)" and "tc-DNA AON SMN2i7(10;25)", respectively) effectively mediates the inclusion of exon 7 in SMN2 in fibroblast cells (G03813 cell line) isolated from an SMA patient.

```
tc-DNA AON SMN2i7(10;25):
                              (SEQ ID NO: 5)
5'-CUUUCAUAAUGCUGG-3' tc-DNA AON SMN2e7(39;51):
                              (SEQ ID NO: 6)
5'-UUAAUUUAAGGAA-3'
```

The G03813 cell line originates from a 3-year-old type I SMA patient with two copies of SMN2. GM03813 cells were cultured in Dulbecco's Modified Eagle Medium (DMEM) with 20% fetal bovine serum and 1% penicillin-streptomycin (100 U/ml). tcDNA AON (tc-DNA AON SMN2i7(10;25) and tc-DNA AON SMN2e7(39;51)) transfections were carried out with Oligofectamine (Invitrogen) in medium without serum and antibiotics for 48 hours. Total RNA was extracted 48 hours post transfection using TRIzol reagent (Invitrogen) and first-strand cDNA synthesis was performed using SuperScript II (Invitrogen) and random hexamers. PCR was carried out using Master Mix 2× Phusion GC (Finnzymes) in a total volume of 50 µL with 11 µL of cDNA and 10 µM each of SMN-Ex6-FW and SMN-Ex8-Re primers. PCR products were then separated by electrophoresis on a 3% agarose gel.

```
SMN-Ex6-Fw
5'-GCTGATGCTTTGGGAAGTATGTA-3'

SMN-Ex8-Re
5'-ATTCCAGATCTGTCTGATCG-3'
```

The data presented in FIG. 19 show that both tc-DNA AON SMN2c7(39;51) and tc-DNA AON SMN2i7(10;25) promote exon 7 inclusion in SMN2 mRNA. Panel A shows RT-PCR analysis of RNA from GM03813 cells treated with the indicated tc-DNA oligonucleotides. The intensity of the band corresponding to SMN2 without exon 7 ("SMN2 (Δ7)") is lower with both tc-DNA oligonucleotides (lanes 3 and 4) compared to the band in the untreated lane (lane 2). Panel B is a normalized quantification plot of the gel showing that upon tc-DNA AON transfection, the upper band corresponding to SMN1 +full length SMN2 increased, while the lower band corresponding to SMN2 (Δ7) significantly decreased.

Panel C shows a Western blot of lysates from wild type fibroblasts and GM03813 cells transfected with the indicated tc-DNA oligonucleotides. Protein extracts were obtained in lysis buffer (10 mmol/l HEPES pH 7.9, 100 mmol/l KCl, 1 mmol/l EDTA, 1 mmol/l 1,4-dithiothreitol, 1× complete protease inhibitor cocktail (Roche), 0.5% NP-40). Equal amounts of protein (determined by Bradford Protein Assay (Pierce)) were mixed with 2× loading buffer (125 mmol/l Tris pH 6.8, 2% sodium dodecyl sulfate, 10% glycerol, 0.01% bromophenol blue, 10% β-mercaptoethanol) and protein concentration was determined using the Bradford Protein Assay (Pierce). Ten micrograms of each protein sample were resolved by SDS-PAGE 4-12% Bis-Tris Gels (Invitrogen) and transferred onto a nitrocellulose membrane. The membrane was blocked with 10% milk in PBS-Tween buffer, probed with a rabbit polyclonal SMN antibody (dilution 1:500; h-195, Santa Cruz) which recognizes SMN1, SMN2, and the truncated form of SMN2, and then incubated with a goat anti-rabbit secondary antibody conjugated with horseradish peroxidase (1:50,000). Signals were detected with the SuperSignal West Pico Chemiluminescent kit (ThermoScientific). To confirm equal loading of proteins, the membrane was washed, reblocked, and probed with a mouse monoclonal anti-actin antibody, followed by incubation with a secondary sheep anti-mouse antibody conjugated with horseradish peroxidase (1:15,000). Signals were detected as described above. Lane 1: GM03813 cells transfected with tc-DNA AON SMN2i7 (10;25); Lane 2: GM03813 cells transfected with tc-DNA AON SMN2e7(39; 51); Lane 3: GM03813 cells transfected with both tc-DNA AON SMN2i7(10;25) and tc-DNA AON SMN2e7(39;51); Lane 4: wild type fibroblasts; Lane 5: Non-transfected GM03813 cells.

The data in panel C indicate transfection with tc-DNA oligonucleotides rescued SMN levels in GM03813 cells due to inclusion of exon 7 in SMN2 mRNA. Control GM03813 cells display some SMN protein due to sporadic natural inclusion of exon 7 in SMN2.

Panel D shows a photomicrograph of GM03813 cells transfected with 30 µg tc-TSL and subsequently stained with SMN antibody. Transfected GM03813 cells on slides were fixed with acetone/methanol (volume/volume). Fixed cells were blocked in PBS+5% BSA for 1 hour, followed by incubation with a rabbit polyclonal SMN antibody (1:100 in PBS+1% BSA; h-195, Santa Cruz) for 1 hour. Cells were washed in PBS and incubated with a secondary anti-rabbit antibody conjugated to Alexa 594 for 1 hour. Cells were then washed in PBS and incubated with DAPI (1:50,000) for 5 minutes. Slides were fitted with coverslips using Fluoromount-G (SouthernBiotech) and incubated overnight at 4° C. The photomicrograph shows that SMN (red) levels increased in the nuclei (blue) of GM03813 cells transfected with tc-DNA TSL.

Example 9

Tricyclo-DNA Antisense Oligonucleotides Directed to CUG Repeats Reduce Mutant DMPK mRNA Expression in DM1 Myoblasts This example demonstrates that tc-DNA AON designed for CUG repeats in mutant DMPK mRNA having the sequence 5'-CAGCAGCAGCAGCAGCAGCAG'3' ("tc-DNA AON DM1(CAG7)"; SEQ ID NO: 9) effectively reduces the expression of mutant DMPK mRNA with 800 CUG repeats in human DM1 myoblasts isolated from muscle biopsy obtained from the Tissue Bank for Research "Myobank".

DM1 myoblasts were transfected with increasing amounts of tc-DNA AON DM1(CAG7) (0, 3.5 µg, 10 µg, and 20 µg) using Lipofectamine (Invitrogen). Three days after transfection, the expression of wild type and mutant DMPK mRNAs were detected by Northern blot. Briefly, 5-10 µg of total RNA were separated on 1.3% agarose MOPS-gels containing 0.66 M formaldehyde and transferred onto Hybond-N+ membranes (Amersham Pharmacia Biotech) by capillary transfer with 10X SSC. Blots were hybridized with a random-primed $^{32}$P-labeled (Bgl II-Sac I fragment of DMPK cDNA) probe in hybridization buffer (2% SDS, 10% dextran sulfate, 1× SSPE, 100µg/ml salmon sperm DNA, 2% Denhart's) at 68° C. overnight. Signals were analyzed on a phospho-imager (Molecular Imager FX, Bio-Rad) and quantified using Quantity One (Bio-Rad).

Figure 20A:
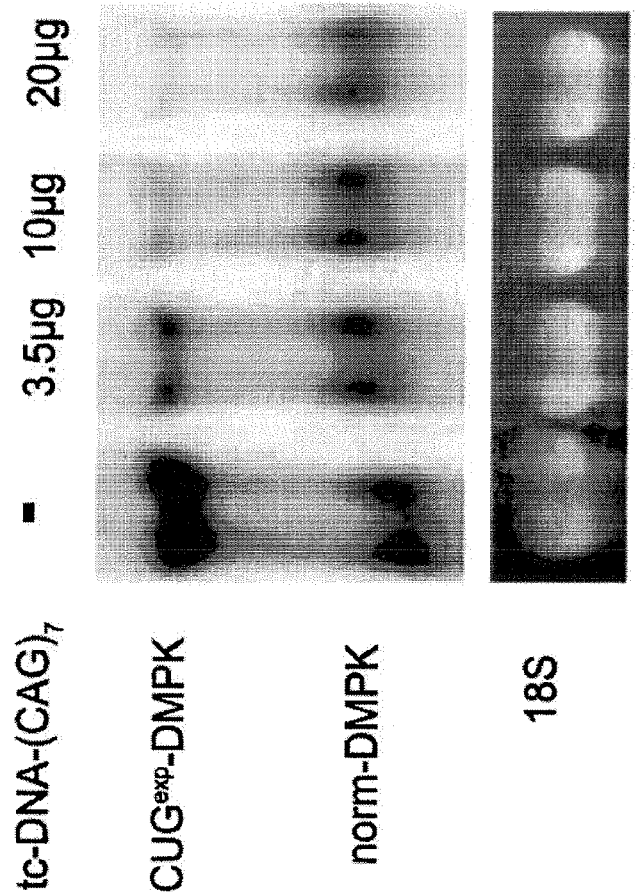
FIG. 20A is a Northern blot showing decreasing levels of mutant human DMPK mRNAs with increasing amounts of tc-DNA AON DM1 (CAG7) (referred to as tc-DNA (CAG)$_7$) transfected into DM1 myoblasts in vitro. After 3 days, cultures were harvested and processed for mRNA extraction and Northern blot analysis.
Figure 20B:
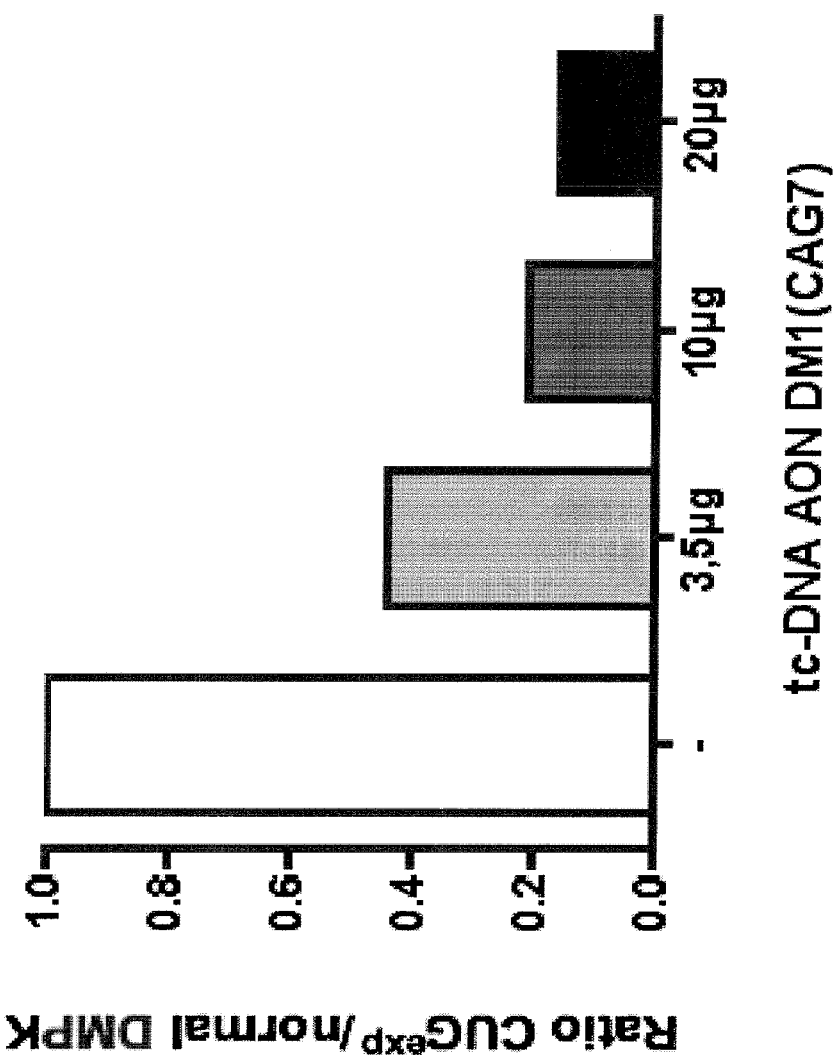
FIG. 20B is a quantification plot reflecting the ratio of mutant DMPK to normal DMPK mRNAs.
Figure 21A:
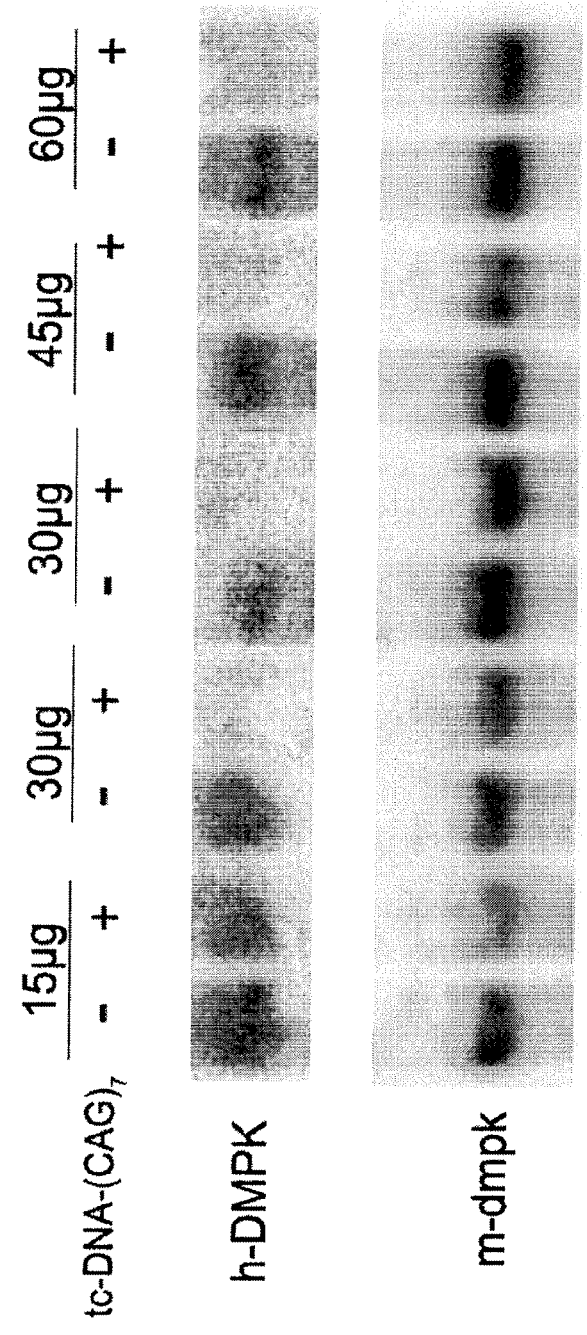
FIG. 21A is a Northern blot showing decreasing levels of mutant human DMPK mRNAs with increasing amounts of tc-DNA AON DM1 (CAG7) (referred to as tc-DNA (CAG)$_7$), with the sequence 5'-CAGCAGCAGCAGCA-GCAGCAG-3' (SEQ ID NO: 9), injected into TA muscles of DM1 mice expressing human DMPK mRNA with 700 CUG repeats.
Figure 21B:
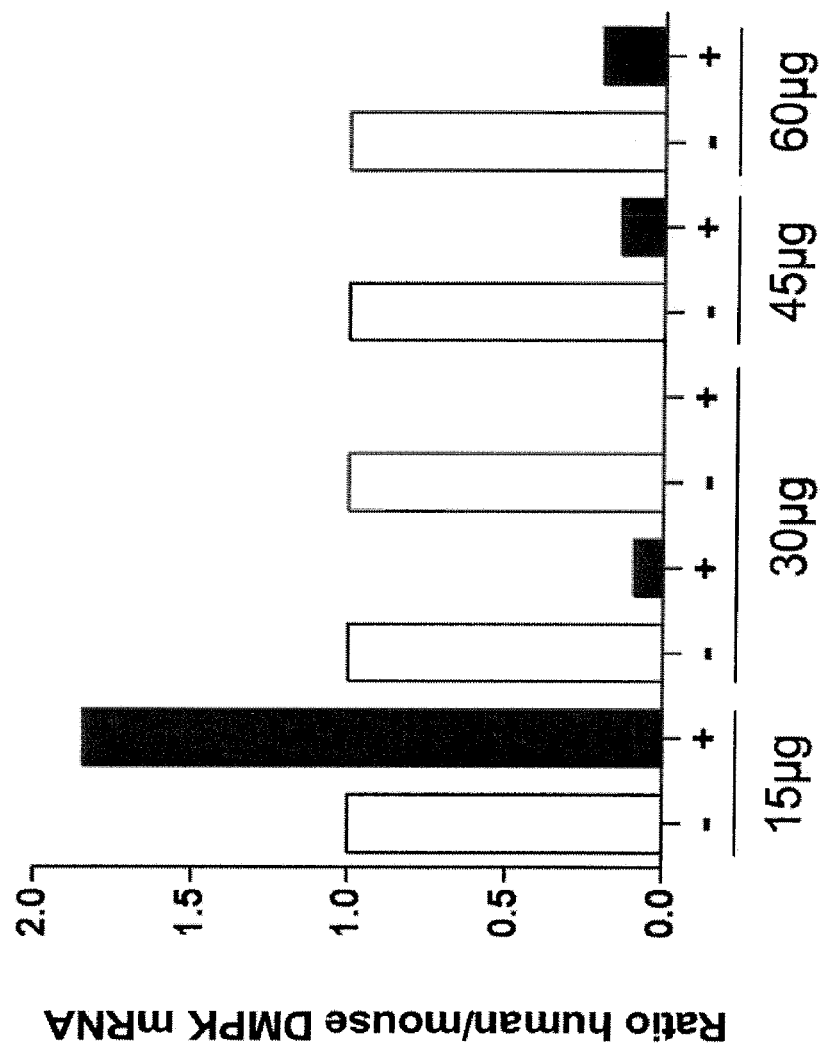
FIG. 21B and FIG. 21D are quantification plots reflecting the ratio of mutant human DMPK to mouse DMPK mRNAs in Northern blots from FIG. 21A and FIG. 21C, respectively.
Figure 21C:
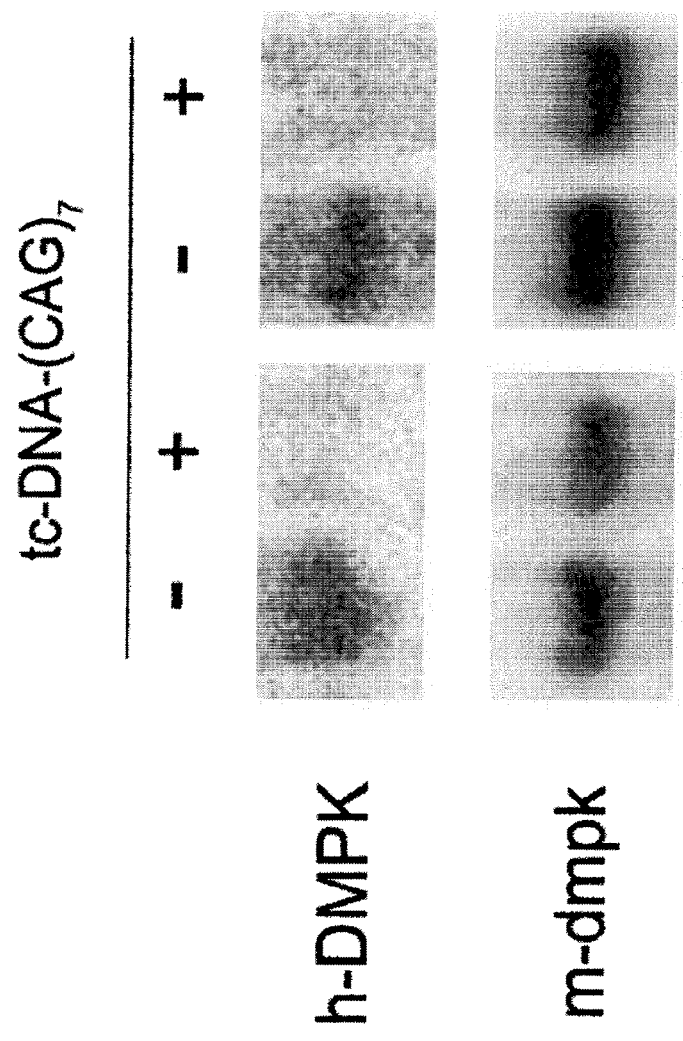
FIG. 21C is a Northern blot showing decreased levels of mutant human DMPK mRNAs when 30 or 60 μg of tc-DNA AON DM1(CAG7) was injected into TA muscles of DM1 mice (n=4).
Figure 21D:
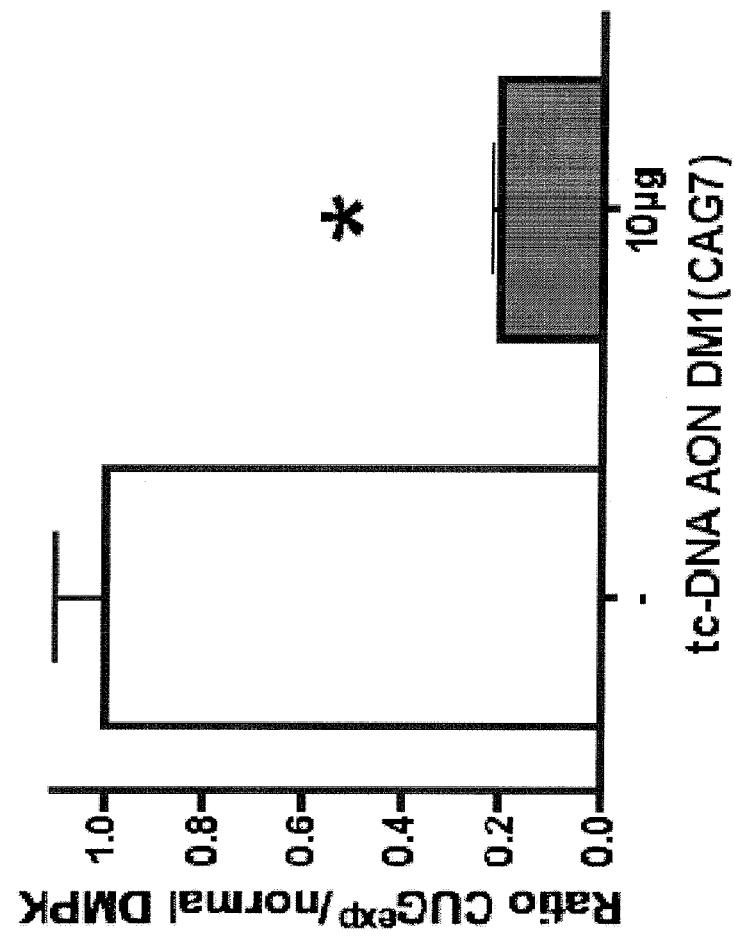

Panel A of FIG. 20 shows that levels of mutant DMPK decreased with increasing amounts of transfected tc-DNA AON DM1(CAG7). Importantly, levels of wild type DMPK were unaltered. 18S RNA was used as a loading control. Panel B is a quantification plot of the Northern blot from Panel A. Quantification was performed by measuring the band intensity ratio of mutant DMPK to wild type DMPK.

Example 10

Tc-DNAs Directed to CUG Repeats Reduce Mutant DMPK mRNA Expression in DM1 Mice

This example demonstrates that tc-DNA AON DM1 (CAG7) effectively reduces levels of mutant human DMPK mRNA with 700 CUG repeats expressed in TA muscles of DM1 mice.

TA muscles of DM1 mice expressing human DMPK mRNA with 700 CUG repeats were injected with increasing amounts of tc-DNA AON DM1(CAG7). One week later, total RNA was extracted using TRIzol reagent (Invitrogen). Human DMPK and mouse DMPK mRNAs were detected by Northern blot. Briefly, 8-10 µg of total RNA were separated on 1.3% agarose MOPS-gels containing 0.66 M formaldehyde and transferred onto Hybond-N+membranes (Amersham Pharmacia Biotech) by capillary transfer with 10× SSC. Blots were hybridized with a random-primed $^{32}$P-labeled (Bgl II-Sac I fragment of DMPK cDNA) probe in hybridization buffer (2% SDS, 10% dextran sulfate, 1× SSPE, 100 µg/ml salmon sperm DNA, 2% Denhart's) at 68° C. overnight. Signals were analyzed on a phospho-imager (Molecular Imager FX, Bio-Rad) and quantified using Quantity One (Bio-Rad).

Panels A and C of FIG. 21 show that levels of mutant human DMPK decreased with increasing amounts of transfected tc-DNA AON DM1(CAG7). Panels B and D are quantification plots of Northern blots from Panels A and C, respectively. Quantification was performed by measuring the band intensity ratio of mutant human DMPK to wild type mouse DMPK.

* * *

While the disclosure has been described in each of its various embodiments, it is expected that certain modifications thereto may be undertaken and effected by the person skilled in the art without departing from the true spirit and scope of the disclosure, as set forth in the previous description and as further embodied in the following claims. The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims. It is further to be understood that all values are approximate, and are provided for description.

All U.S. patents, U.S. patent application publications, U.S. patent applications, foreign patents, foreign patent applications, non-patent publications, figures, tables, and websites referred to in this specification are expressly incorporated herein by reference, in their entirety.

SEQUENCE LISTING

SEQ ID NO: 1
Artificial Sequence
DNA
Length: 15
tc-DNA AON M23D (+02-13)
aacctcggcttacct SEQ ID NO: 2
Artificial Sequence
DNA
Length: 15
tc-DNA AON H51 (+68+82)
agaaatgccatcttc SEQ ID NO: 3
Artificial Sequence
DNA
Length: 15
tc-DNA AON H51 (+70+84)
aaatgccatcttcct SEQ ID NO: 4
Artificial Sequence
DNA
Length: 15
tc-DNA AON H51 (+73+87)
tgccatcttccttga SEQ ID NO: 5
Artificial Sequence
DNA
Length: 15
tc-DNA AON SMN2i7 (10;25)
cuuucauaaugcugg SEQ ID NO: 6
Artificial Sequence
DNA
Length: 13
tc-DNA AON SMN2e7 (39;51)
uuaauuuaaggaa SEQ ID NO: 7
Artificial Sequence
DNA
Length: 12-21
tc-DNA AON DM1(CAG$_n$)
(cag)$_n$ n = 4-7

SEQ ID NO: 8
Artificial Sequence
DNA
Length: 15
tc-DNA AON DM1(CAG5)
cagcagcagcagcag SEQ ID NO: 9
Artificial Sequence
DNA
Length: 21
tc-DNA AON DM1(CAG7)
cagcagcagcagcagcagcag

The invention claimed is:

1. A method for the delivery of an antisense oligonucleotide (AON) into a human patient comprising administering to the patient a tricyclo-DNA (tc-DNA) antisense oligonucleotide (AON),
wherein the tc-DNA AON has a length of 10 to 18 nucleotides, wherein all the nucleotides of the tc-DNA AON are tc-DNA nucleotides;
wherein the tc-DNA AON comprises a sequence of nucleotides that is complementary to an intron-exon junction; and
wherein the administration of the tc-DNA AON to the patient results in increased exon skipping at the intron-exon junction in the patient.

2. The method of claim 1, wherein the tc-DNA AON comprises a sequence of nucleotides that is complementary to an intron-exon junction within a mutated dystrophin pre-mRNA.

3. The method of claim 2, wherein the administration of the tc-DNA AON to the patient results in increased skipping of exon 23 in the patient.

4. The method of claim 2, wherein the wherein the administration of the tc-DNA AON to the patient results in increased skipping of exon 51 in the patient.

5. The method of claim 1, wherein the tc-DNA AON has a length of 12 to 16 nucleotides.

6. The method of claim 1, wherein the tc-DNA AON has a length of 13 to 15 nucleotides.

7. The method of claim 1, wherein the administration comprises intramuscular (i.m.), intravenous (i.v.), intraperitoneal (i.p.), intra-arterial, sub-cutaneous or transdermic injection of the tc-DNA AON.

8. The method of claim 1, comprising administering 1 mg/kg to 100 mg/kg body weight/day to the patient.

9. The method of claim 1, comprising injecting the tc-DNA AON directly into the muscle of the patient.

10. The method of claim 1, wherein 8-16 nucleotides of said tc-DNA AON are complementary to a dystrophin pre-mRNA intronic splice donor site, wherein 2-8 nucleotides of said tc-DNA AON are complementary to a dystrophin pre-mRNA exonic region, and wherein said exonic region is contiguous with and 3' to said intronic splice donor site.

11. The method of claim 1, wherein the tc-DNA AON comprises the nucleotide sequence 5'-AACCTCGGCTTACCT-3' (SEQ ID NO: 1).

12. The method of claim 1, wherein the tc-DNA AON is complementary to the nucleotide sequence 5'-AGAAATGCCATCTTC-3' (SEQ ID NO: 2).

13. The method of claim 1, wherein the tc-DNA AON is complementary to the nucleotide sequence 5'-AAATGCCATCTTCCT-3' (SEQ ID NO: 3).

14. The method of claim 1, wherein said tc-DNA AON is complementary to the nucleotide sequence 5'-TGCCATCTTCCTTGA-3' (SEQ ID NO: 4).

15. The method of claim 1, wherein the patient has Duchene Muscular Dystrophy (DMD).

\* \* \* \* \*